(12) United States Patent
Pizzi et al.

(10) Patent No.: US 12,109,564 B2
(45) Date of Patent: Oct. 8, 2024

(54) MICRO-FLUIDIC DEVICE FOR CONCENTRATION OF PARTICLES VIA CENTRIFUGAL FORCE, AND CORRESPONDING CENTRIFUGATION AND/OR DETECTION DEVICE

(71) Applicant: ELTEK S.p.A., Casale Monferrato (IT)

(72) Inventors: Marco Pizzi, Casale Monferrato (IT); Giovanni Melioli, Casale Monferrato (IT); Valentina Gallo, Casale Monferrato (IT); Massimo Zanin, Casale Monferrato (IT)

(73) Assignee: ELTEK S.p.A., Casale Monferrato (IT)

( * ) Notice: Subject to any disclaimer, the term of this patent is extended or adjusted under 35 U.S.C. 154(b) by 955 days.

(21) Appl. No.: 16/972,283

(22) PCT Filed: Jun. 5, 2019

(86) PCT No.: PCT/IB2019/054679
§ 371 (c)(1),
(2) Date: Dec. 4, 2020

(87) PCT Pub. No.: WO2019/234654
PCT Pub. Date: Dec. 12, 2019

(65) Prior Publication Data
US 2021/0237062 A1 Aug. 5, 2021

(30) Foreign Application Priority Data
Jun. 6, 2018 (IT) .................. 102018000006083

(51) Int. Cl.
*B01L 3/00* (2006.01)
*C12Q 1/18* (2006.01)
(52) U.S. Cl.
CPC .......... *B01L 3/502753* (2013.01); *C12Q 1/18* (2013.01); *B01L 2200/0668* (2013.01);
(Continued)

(58) Field of Classification Search
CPC ....... B01L 3/502753; B01L 2200/0668; B01L 2300/0645; B01L 2300/0806;
(Continued)

(56) References Cited

U.S. PATENT DOCUMENTS

| 2003/0044322 A1* | 3/2003 | Andersson ....... G01N 35/00069 366/150.1 |
| 2004/0038426 A1* | 2/2004 | Manalis ........... G01N 33/54366 436/514 |

(Continued)

FOREIGN PATENT DOCUMENTS

| CN | 102227637 A | 10/2011 |
| CN | 107051305 A | 8/2017 |

(Continued)

OTHER PUBLICATIONS

International Search Report and Written Opinion of the ISA for PCT/IB2019/054679, mailed Sep. 23, 2019, 14 pages.

(Continued)

*Primary Examiner* — P. Kathryn Wright
*Assistant Examiner* — Curtis A Thompson
(74) *Attorney, Agent, or Firm* — Nixon & Vanderhye P.C.

(57) ABSTRACT

A microfluidic device for concentrating particles contained in a fluid sample (FS) comprises a substrate (11) configured for being set in rotation about a centre of rotation (5a), the substrate (11) having a surface (11b) defined in which is at least one microfluidic arrangement (12) that extends substantially according to a plane identified by the substrate (11). The at least one microfluidic arrangement (12) comprises at least one microchannel (13) having a first end (13a) and a second end (13b), wherein: —the at least one microchannel (13) comprises, in a region thereof intermediate between its first end (13a) and its second end (13a), at least one accumulation area (15) that is at a first distance (R1) in (Continued)

a radial direction (R) from the centre of rotation (5a) of the substrate (11); —the first end (13a) and the second end (13b) of the at least one microchannel (13) are at second distances (R2) in a radial direction (R) from the centre of rotation (5a) of the substrate (11); and —the first distance (R1) in a radial direction (R) is greater than the second distances (R2) in a radial direction (R), in such a way that particles (P) possibly contained in a volume of fluid of the fluid sample (FS) that penetrates into the at least one microchannel (13) tend to concentrate in the at least one accumulation area (15) as a result of the centrifugal force caused by a rotation of the substrate (11) about the centre of rotation (5a).

15 Claims, 16 Drawing Sheets

(52) U.S. Cl.
CPC .................. *B01L 2300/0645* (2013.01); *B01L 2300/0806* (2013.01); *B01L 2300/161* (2013.01)

(58) Field of Classification Search
CPC ....... B01L 2300/161; B01L 2300/0861; C12Q 1/18; G01N 2001/4083; G01N 2035/00495; G01N 35/00069; G01N 1/4077
See application file for complete search history.

(56) References Cited

U.S. PATENT DOCUMENTS

| | | |
|---|---|---|
| 2004/0248093 A1 | 12/2004 | Coombs et al. |
| 2007/0275426 A1 | 11/2007 | Wo et al. |
| 2008/0128332 A1* | 6/2008 | Lean .................. B01D 21/2488 209/210 |
| 2008/0227209 A1* | 9/2008 | Deng ..................... G01N 33/92 436/71 |
| 2008/0317634 A1 | 12/2008 | Kido et al. |
| 2010/0062414 A1* | 3/2010 | Yamamoto .......... G01N 33/558 422/68.1 |
| 2012/0040843 A1 | 2/2012 | Ducree et al. |

FOREIGN PATENT DOCUMENTS

| | | |
|---|---|---|
| CN | 107110765 A | 8/2017 |
| EP | 2 817 519 | 7/2016 |
| JP | S60-70462 A | 4/1985 |
| JP | 2003-202321 A | 7/2003 |
| JP | 2004-109082 A | 4/2004 |
| JP | 2011-069674 A | 4/2011 |
| JP | 2011-075420 A | 4/2011 |
| JP | 2014-103966 A | 6/2014 |
| WO | 02/074438 A2 | 9/2002 |
| WO | 2015/131662 | 9/2015 |

OTHER PUBLICATIONS

Office Action dated Nov. 9, 2023, issued in China Patent Application No. 201980053572.7, 10 pages.

* cited by examiner

MICRO-FLUIDIC DEVICE FOR CONCENTRATION OF PARTICLES VIA CENTRIFUGAL FORCE, AND CORRESPONDING CENTRIFUGATION AND/OR DETECTION DEVICE

This application is the U.S. national phase of International Application No. PCT/IB2019/054679 filed 5 Jun. 2019, which designated the U.S. and claims priority to IT Patent Application No. 102018000006083 filed 6 Jun. 2018, the entire contents of each of which are hereby incorporated by reference.

FIELD OF THE INVENTION

The present invention relates in general to techniques for detecting or estimating the amount of particles present in a fluid sample, in particular particles at low concentrations and in small volumes.

The invention has been developed with particular reference to centrifugation supports or substrates and to microfluidic arrangements or devices designed to be subjected to centrifugation, as well as to devices and methods for conducting examinations or analyses on fluid samples containing bacteria or micro-organisms, for example for rapid execution of antibiograms. The invention may in any case also be applied to the detection of other types of particles that may be present in a fluid sample, not necessarily organic or biological fluids or particles.

PRIOR ART

Various techniques are known for counting particles, for example cells, present in a sample of a fluid, for example a biological fluid. The systems most commonly used are of an optical type (with or without fluorescence), of an impedancemetry type, or of a static type by means of image recognition. These known systems in general require relatively large sample amounts and do not enable an efficient parallelisation of the measurement; i.e., they presuppose a considerable amount of starting samples to be able to carry out many measurements in parallel and/or simultaneously. Known systems based upon techniques of image recognition can be used for the analysis of small fluid samples, but do not enable parallelisation of a number of samples, with consequent increase in the measurement times unless investments are made, which, however, frequently prove anti-economic.

AIM AND SUMMARY OF THE INVENTION

In its general terms, the aim of the present invention is to indicate devices and methods that make it possible to carry out, in a simple, rapid, and inexpensive way, separation, and/or accumulation, and/or quantification, and/or identification of particles present at low concentrations and/or in small volumes in fluid samples, enabling in an equally simple and inexpensive way parallelisation between a number of samples, with advantages in terms of time and costs, as well as in terms of efficiency as regards sensitivity and reproducibility.

A further aim of the invention is to indicate methodologies that make it possible to execute antibiograms (when micro-organisms are being measured), i.e., to obtain profiles of susceptibility of a microbe or a bacterium to antibiotics, in relatively short times, indicatively of some hours; an auxiliary aim of the invention is to indicate methodologies that enable simultaneous execution of a plurality of antibiograms.

The above aims are achieved, according to the present invention, by a microfluidic device for the concentration of particles via centrifugation, and by corresponding supports and methods, which presents the characteristics specified in the annexed claims.

In particular, the invention regards a centrifugable microfluidic device, which includes a substrate, provided on which is at least one microfluidic arrangement aimed at the concentration of the particles present in a fluid sample, for the purposes of evaluation or detection of the amount thereof. The microfluidic arrangement comprises at least one microchannel, preferably a plurality of microchannels substantially aligned to one another or set side by side in a radial direction, which is/are able to receive the fluid of the sample and is/are shaped so as to enable—as a result of centrifugation of the substrate—an accumulation of the particles in a precise and limited portion of the microchannel itself. The particles that have accumulated in the aforesaid portion of the microchannel can then be subjected to detection, i.e., to a direct or indirect quantification and/or identification thereof, for example using detection means of an optical type and/or detection means of an electrical type. Preferentially, following upon centrifugation, at least a prevalent part of the fluid sample remains in the microchannel, or at least in its accumulation portion, with the accumulated particles that hence remain immersed in the liquid.

The invention likewise regards centrifugation and/or detection devices, which can be used in combination with the aforesaid microfluidic device, as well as methodologies of analysis based upon the use of such a device.

As will emerge clearly hereinafter, the invention makes it possible to carry out in a simple and rapid way effective detection of amounts of particles in samples of relatively modest volume of the fluid of interest.

BRIEF DESCRIPTION OF THE DRAWINGS

Further aims, characteristics, and advantages of the invention will emerge clearly from the ensuing detailed description, with reference to the annexed drawings, which are provided purely by way of non-limiting example and in which.

DETAILED DESCRIPTION OF EMBODIMENTS

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment", "in one embodiment", "in various embodiments", and the like, that may be present in various points of this description do not necessarily refer to one and the same embodiment. Moreover, particular conformations, structures, or characteristics defined in the framework of the present description may be combined in any adequate way in one or more embodiments, even different from the ones represented. The reference numbers and spatial references (such as "top", "bottom", "upper", "lower", etc.) used herein are provided merely for convenience and hence do not define the sphere of protection or the scope of the embodiments. The same reference numbers are used in the figures to designate elements that are similar or technically equivalent to one another.

Figure 1:
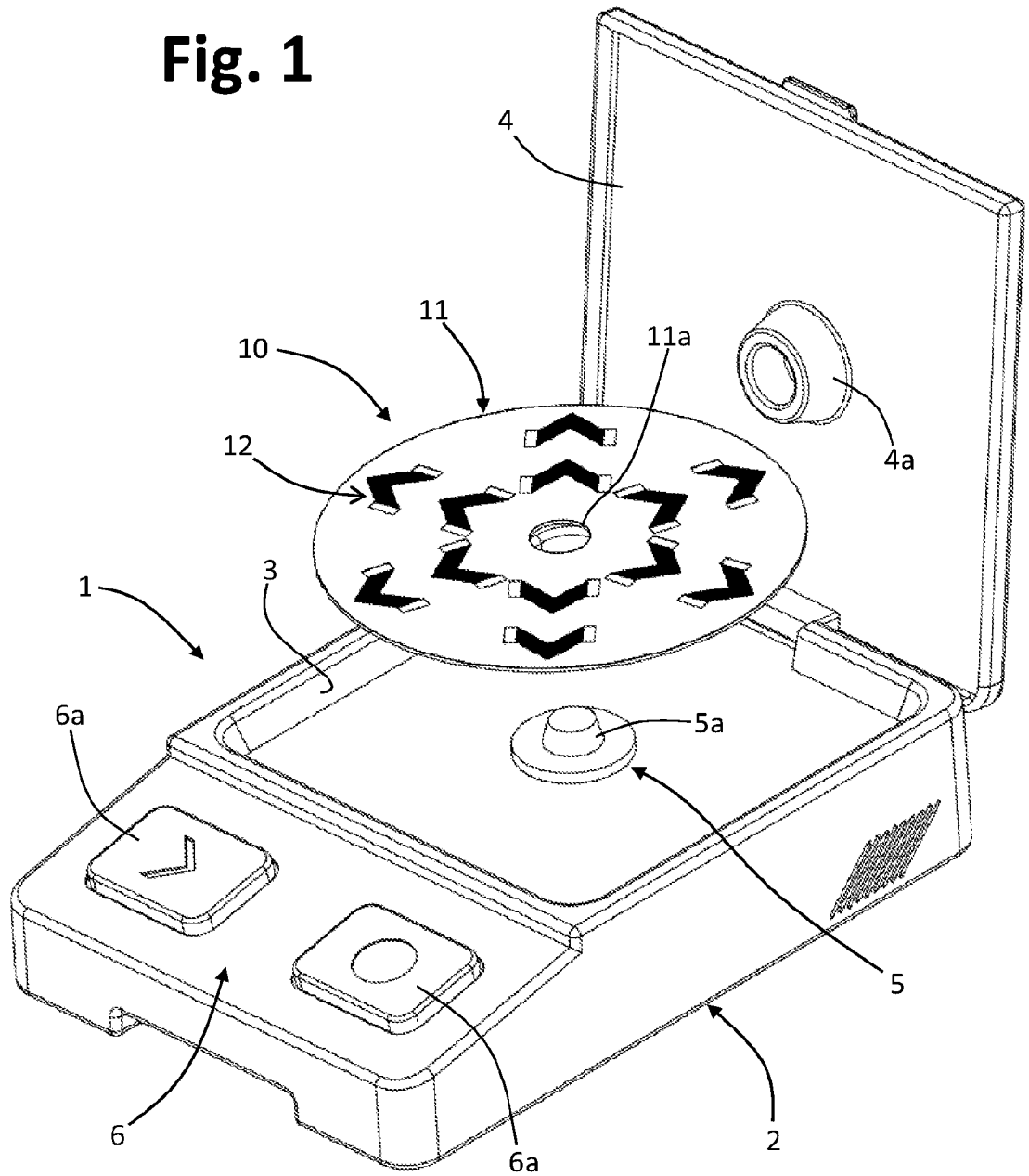
FIG. 1 is a schematic perspective view of a centrifugation device and of a microfluidic device according to possible embodiments of the invention.

With initial reference to FIG. 1, designated as a whole by 1 is a centrifugation device, having a structure 2 that defines a treatment or centrifugation chamber 3. In various embodiments, the device 1 includes a lid or door 4, preferably hinged to the structure 2, for closing the chamber 3. The device 1 has a driving or movement system 5, which includes a rotary member 5a within the chamber 3, designed to set in rotation a centrifugation support, i.e., a centrifugable device. Possibly, there may be associated to the lid 4 a corresponding part 4a of a positioning and/or guide system of the centrifugation support. The aforesaid actuation system 5 preferentially comprises an electric motor, possibly provided with a motor reducer and/or an electronic control circuit. The centrifugation speed may indicatively be higher than 5000 rpm, in the case where the particles being detected are bacteria or micro-organisms of small dimensions, and indicatively higher than 1200 rpm in the case where the particles to be detected are blood cells or body cells.

In various embodiments, the device 1 comprises a system for control of the temperature and/or humidity within the chamber 3. In various embodiments, this system is configured for maintaining a temperature higher than 25° C., preferably between 36° C. and 38° C., and/or a humidity that is preferably higher than 95%. In various preferred embodiments the device 1 comprises a suction system and/or a system for regulation of the pressure, pre-arranged for keeping the centrifugation area, or the chamber 3, at a pressure lower than ambient pressure and/or for forcing a flow of air at output from said area or chamber into a filtering system configured for preventing diffusion of potentially contaminated aerosols into the environment.

In various embodiments, the device 1 includes a control panel 6, located on which are suitable control elements 6a for starting and/or stopping a process of centrifugation, and/or conditioning, and/or pressure regulation, and/or detection, and possibly for setting parameters of the aforesaid process (for example, centrifugation speed and/or time, and/or temperature, and/or humidity, and/or pressure in the chamber 3). The aforesaid control elements may be of any suitable 20 type (pushbuttons, knobs, sliders, a touch display, etc.).

In FIG. 1, designated by 10 is a centrifugable device according to possible embodiments of the invention. In various preferential embodiments, the device 10 is configured for integrating or housing an arrangement designed to concentrate, via centrifugation, particles contained in a sample of a fluid substance, and includes for this purpose a substrate 11 provided with at least one microfluidic arrangement 12: for this reason, in what follows, the device 10 will be identified as "microfluidic device".

The substrate 11 of the device 10 is configured for being set in rotation even at a high speed about a centre of rotation, which is here assumed as being identified by the member 5a of the device 1. For this purpose, in various preferential embodiments, the device 10 is disk-shaped and preferentially includes means 11a for coupling to the actuation system of a corresponding centrifugation device, for example, for coupling to the member 5a of the device 1 of FIG. 1. In the case exemplified, the aforesaid coupling means 11a comprise a central passage or hole in the disk-shaped substrate 11. As will be seen, on the other hand, the disk shape of the substrate 11 does not constitute an essential characteristic, this not discounting the fact that the substrate is to be set in rotation about a centre of rotation.

In various embodiments, the substrate 11 has a relatively small thickness, for example comprised between 0.5 and 4 mm. The substrate may, for example, be made of glass or plastic (for instance, polycarbonate, or polyethylene, or cyclo-olefin copolymers or COCs) and have a diameter indicatively comprised between 10 and 30 cm, or between 6 and 30 cm, preferably between 8 and 10 cm, hence possibly being similar to a classic compact disk. The materials used are preferentially electrically insulating materials, very preferably materials that are at least in part transparent.

Figure 2:
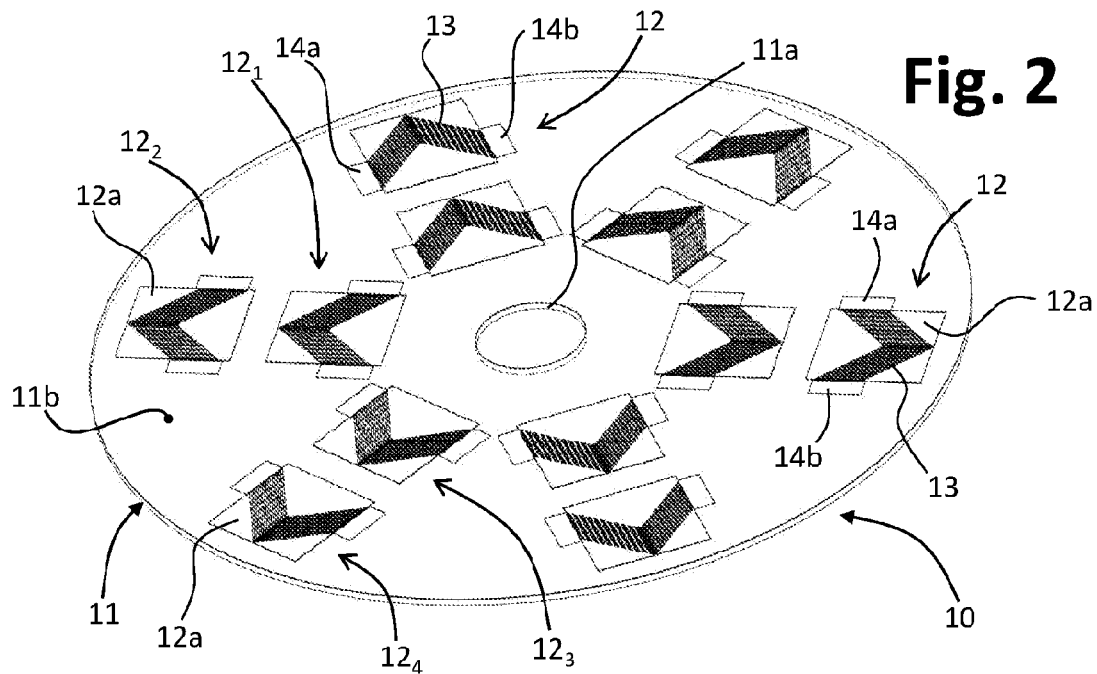
FIG. 2 is a schematic perspective view of a microfluidic device according to possible embodiments of the invention.

With reference also to FIG. 2, the substrate 11 has a surface 11b—referred to herein conventionally as "upper surface"—defined at which is the aforesaid at least one microfluidic arrangement 12. In various preferential embodiments, defined on the surface 11b are a plurality of microfluidic arrangements 12, which are preferably but not necessarily the same as one another. In various embodiments, a number of microfluidic arrangements are substantially aligned with one another in a radial direction, as, for example, the arrangements designated by $12_1$ and $12_2$ in FIG. 2, and/or a number of microfluidic arrangements are set substantially according to a circumference or at one and the same distance from the centre of rotation 11a or 5a, as, for example, the arrangements designated by $12_1$ and $12_3$ or the arrangements designated by $12_2$ and $12_4$ in FIG. 2.

The at least one microfluidic arrangement 12, or each microfluidic arrangement 12, preferentially extends according to a plane identified by the substrate 11, and for this purpose may be defined on the surface 11b via a suitable technique, for instance via micro-etching, or moulding, or polymerisation of resins by means of UV. Not excluded from the scope of the invention is formation of the microchannels via deposition of material on the substrate 11.

The at least one microfluidic arrangement 12 comprises at least one microchannel 13 having two opposite ends, which is pre-arranged for receiving a sample fluid. Preferentially, but not necessarily, the arrangement 12 also comprises at least one chamber 14a or 14b (which may also be in the form of a duct or channel), connected in fluid communication to which is one of the two aforesaid ends of the at least one microchannel 13. In various preferential embodiments, two chambers 14a and 14b are provided, connected in fluid communication to each of which is a respective end of the at least one microchannel 13.

In various preferred embodiments, each arrangement 12 comprises a plurality of microchannels 13, which preferentially, but not necessarily, have one of the respective first end and the respective second end connected in fluid communication to one said chamber, for example one of the first chamber 14a and the second chamber 14b. In what follows, reference will be made to embodiments that comprise one said plurality of microchannels 13.

In various embodiments, the first or second ends of a plurality of microchannels 13 are connected in fluid communication to one and the same chamber, for example, the chamber 14a or the chamber 14b. Preferably, the first ends of the microchannels 13 of the plurality are connected in parallel to a first chamber, for example, the chamber 14a, and the second ends of the microchannels 13 of the plurality are connected in parallel to a second chamber, for example, the chamber 14b: this, however, does not constitute an essential characteristic of the invention for the reasons explained hereinafter. In various embodiments, the chambers 14a and 14b are in generally mutually opposed positions so that the microchannels 13 extend at least in part in a position intermediate between them.

The microchannels of an aforesaid plurality are preferably at least in part the same as one another and/or extend at least in part substantially parallel to or equidistant from one another, preferably parallel to or equidistant from one another in a radial direction of the substrate. In various embodiments, microchannels are provided that are substantially the same as one another in terms of shapes and size, whereas in other embodiments, microchannels are provided substantially having one and the same pattern, but having lengths different from one another.

In various embodiments, the microfluidic arrangement 12, or each microfluidic arrangement, comprises a covering element 12a, which covers at least in part the corresponding microchannels 13. Preferentially, the covering element 12a is made at least in part of a transparent material, for example, glass or a plastic material in order to enable viewing of the underlying microchannels 13 for the purposes of optical detection.

Figure 3:
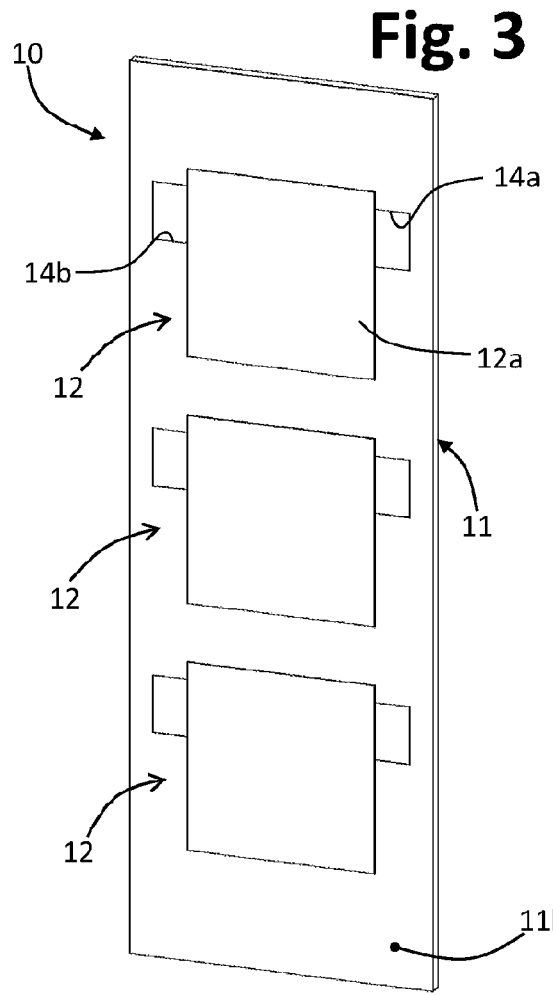
FIGS. 3 and 4 are schematic perspective views of microfluidic devices according to possible embodiments of the invention.

Such a covering element 12a is clearly visible, for example, in FIG. 3, where provided on one and the same device 10 are three microfluidic arrangements 12 aligned in a radial direction (with respect to a centre of rotation of the substrate 11). Each arrangement 12 comprises a corresponding covering element 12a, which overlies the corresponding microchannels 13, leaving, instead, exposed at least one of the lateral chambers 14a, 14b, preferably both of them. The microchannels 13 may be seen in FIG. 4, where the representation of the covering elements 12a has been omitted.

The material of which the covering element 12a, or each covering element 12a, is made is preferably hydrophilic, to facilitate entry of the fluid by capillarity in each microchannel 13. The material of which the microchannels 13 are made, or the material of the substrate 11, may in this case also be a hydrophobic material. It is also preferable for at least one surface of the microchannel 13 that extends throughout the whole length of the microchannel 13 to be made of hydrophilic material: for example, in a microchannel 13 with rectangular or trapezial cross section, at least one of the four walls that define the section of the microchannel will preferably be made of hydrophilic material, for instance, the covering element 12a.

Also the substrate 11 may be made at least in part of a transparent material to enable viewing of the microchannels (for example, in the case where the element 12a is opaque) and/or to enable back-lighting of the microchannels (for example, in the case where the element 12a is transparent). Consequently, both the substrate 11 and the covering elements 12a could be transparent.

In various embodiments, each microchannel has, throughout its whole extent, at least a continuous portion of inner surface having hydrophilic characteristics. The continuity of a hydrophilic portion along an inner wall of the microchannel is useful in the filling step, which envisages, for example, deposition of a drop of the sample liquid in one of the two chambers 14, for example the chamber 14a. Contact with the hydrophilic portion causes filling of the microchannels by capillarity. Once each microchannel is entirely filled, it is no longer subject to flow of liquid inside it, provided that at the bottom (i.e., when it has reached the chamber 14b) the fluid encounters hydrophobic surfaces: in this way, even if contiguous microchannels were to be filled with the sample liquid at different speeds, the microchannel that is filled first would in any case stop the flow of the liquid once the latter has reached the bottom, preventing the liquid from penetrating into the adjacent microchannel or microchannels before they are completely filled (which is to be avoided in so far as the liquid would close the microchannel that is not yet completely full, trapping air bubbles). A way to obtain this effect is, for example, to make the bottom wall and the side walls of the microchannels 13 and the chambers 14 of a single hydrophobic material and to make the upper walls of the microchannels (for example, the walls formed by the covering element 12a) of hydrophilic material, for example glass, taking care to terminate said top walls (for example formed by a covering element 12a made of glass) slightly before the chamber where the liquid is to arrive, for example the chamber 14b, leaving the side walls of the microchannels without covering for at least a few micrometres. If, instead, an upper wall (for example, the covering element 12a) were to terminate partially overlying the chamber 14b where the liquid is to arrive, the microchannel that by capillarity has filled up first would find a hydrophilic path to be able to penetrate into the adjacent channel: if the latter were not yet full of liquid, the flow would be stopped and filling would be incomplete.

As mentioned previously, the substrate 11 of a device 10 does not necessarily have to be disk-shaped. Such a case is exemplified, in fact, in FIGS. 3 and 4, where the substrate designated by 11 has a substantially parallelepipedal, preferably planar, shape (for greater clarity, the representation of the elements 12a has been omitted in FIG. 4). Substrates of this sort, i.e., not disk-shaped ones, may advantageously be pre-arranged for being housed or fixed—for example, via suitable adapter elements—on an intermediate support or in a rack of a centrifugation device of a commercial type, or else on a generic disk-shaped support that is to be coupled to the rotary member 5a of the device 1 of FIG. 1.

Figure 4:
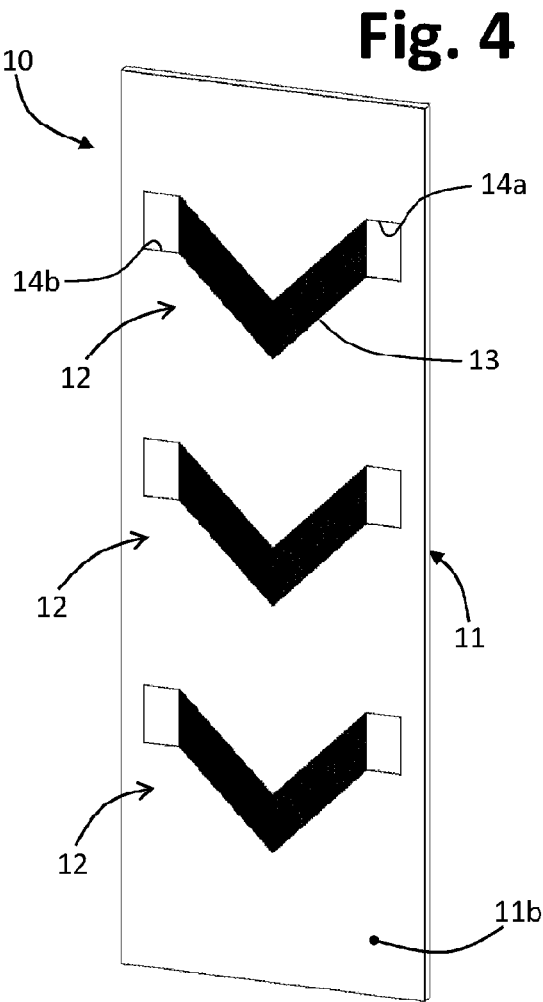

FIGS. 3 and 4 may, however, be understood as representing portions of a larger device 10, for example rectangular portions of a disk-shaped support of the type illustrated in FIG. 2.

Figure 5:
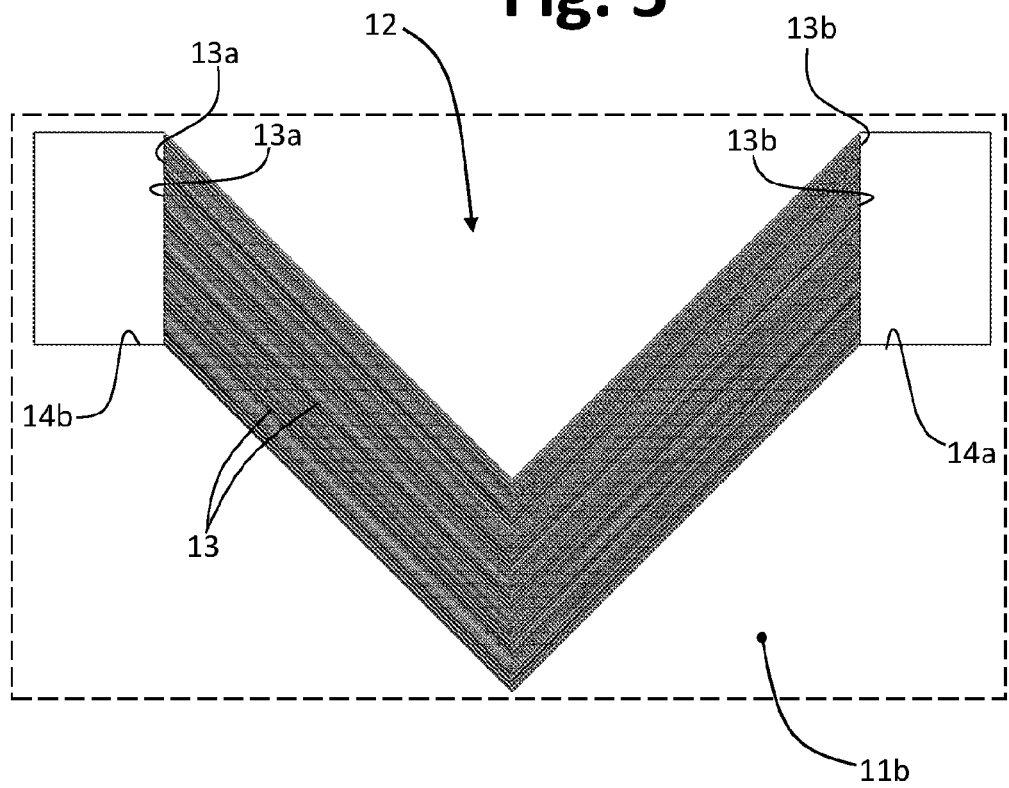
FIG. 5 is a schematic view in front elevation of a microfluidic arrangement according to possible embodiments of the invention.
Figure 6:
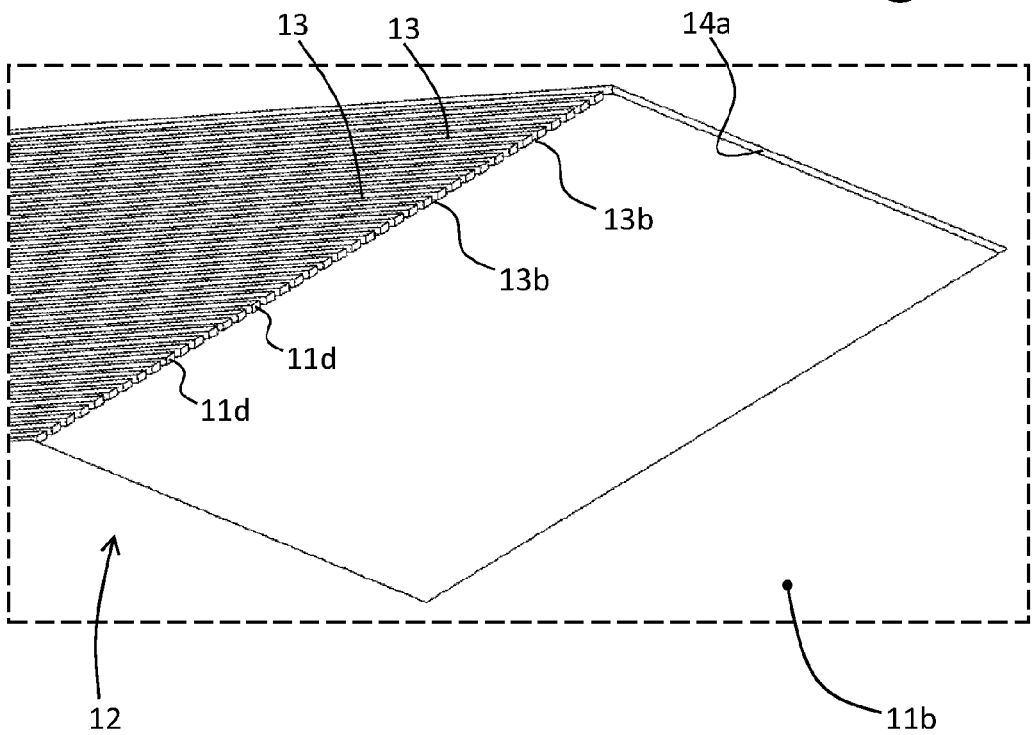
FIG. 6 is a schematic perspective view of an end portion of a microfluidic arrangement according to possible embodiments of the invention.

In FIG. 5, a microfluidic arrangement 12 is represented schematically in front view, without the corresponding covering element 12a, where designated by 13a and 13b are the ends of some microchannels 13, which open at the lateral chambers 14a and 14b, respectively. This characteristic may be appreciated also from FIG. 6, which illustrates a chamber 14a, it being taken for granted that the chamber 14b is preferably built in a similar way. From FIG. 6 it may hence be noted how, in various preferential embodiments, both the lateral chambers 14a (and 14b) and the microchannels 13 are obtained by cavities or surface etchings made in the substrate 11, the microchannels 13 being, in particular, in the form of micro-grooves.

In general terms, each microchannel 13 may have a width of between 5 and 200 μm, preferably between 15 and 50 μm, and/or a depth or height of between 2 and 100 μm, preferably between 5 and 40 μm. The length of each microchannel 13—understood as the distance between its two ends 13a, 13b—may indicatively be between 5 and 50 mm. It is preferable for the microchannels to have a constant section of passage, for homogeneity of analysis.

Figure 7:
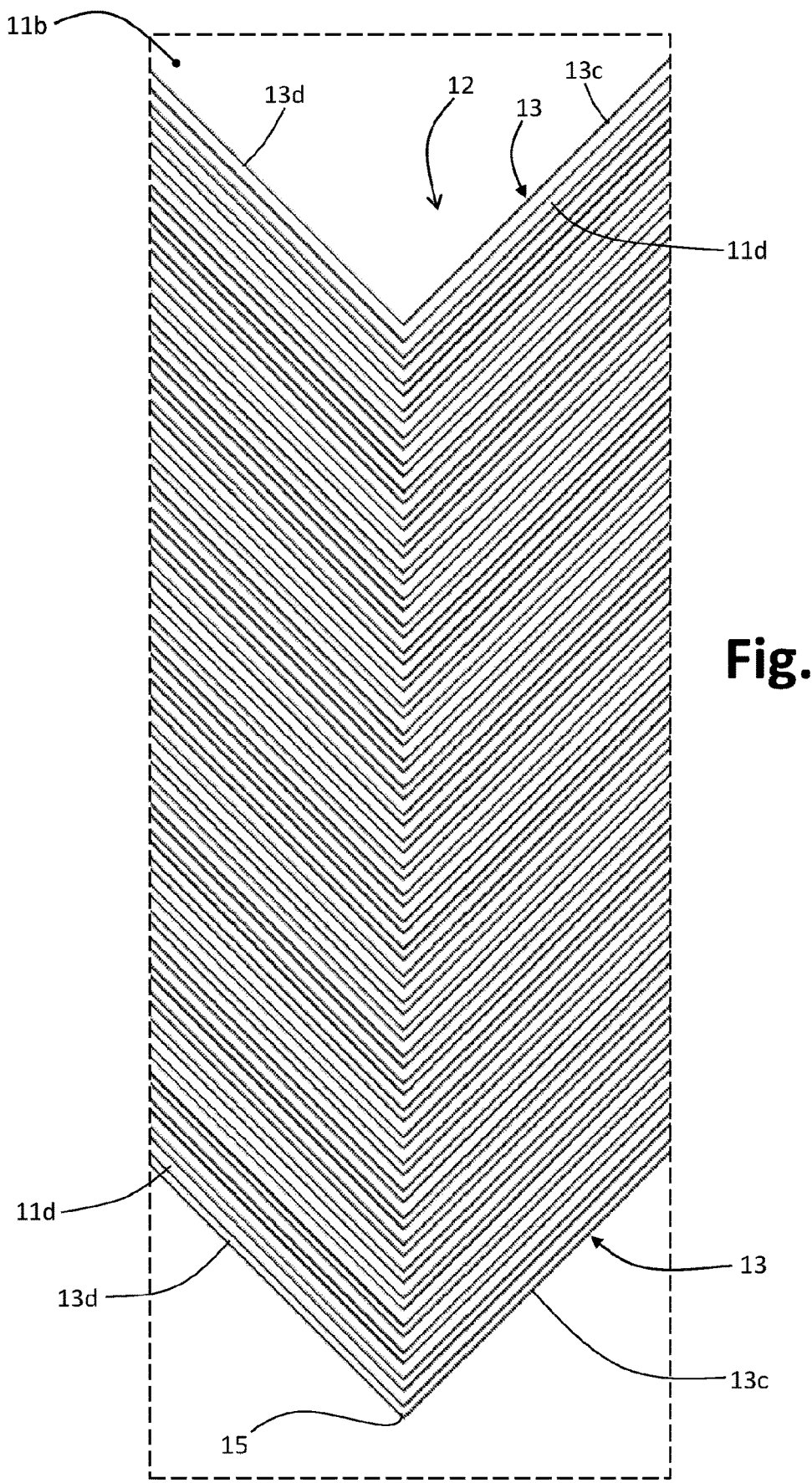
FIG. 7 is a schematic view in front elevation of a central portion of a microfluidic arrangement according to possible embodiments of the invention.

FIG. 7 shows a detail of an intermediate region of a microfluidic arrangement 12, and in particular a central region of the microchannels 13, defined or separated by walls or portions in relief 11d of the substrate 11.

In various preferential embodiments, each microchannel 13 comprises at least two generally convergent microchannel branches, designated in FIG. 7 by 13c and 13d, respectively. This preferential characteristic may be noted also from the schematic example of an arrangement 13 illustrated in FIG. 8 where, for needs of greater clarity, the length of the microchannels 12 has been considerably reduced. In the example, the two microchannel branches 13c and 13d are inclined in opposite directions, with a substantially specular arrangement. In various embodiments, the two microchannel branches 13c and 13d have one and the same section of passage for the liquid.

Figure 8:
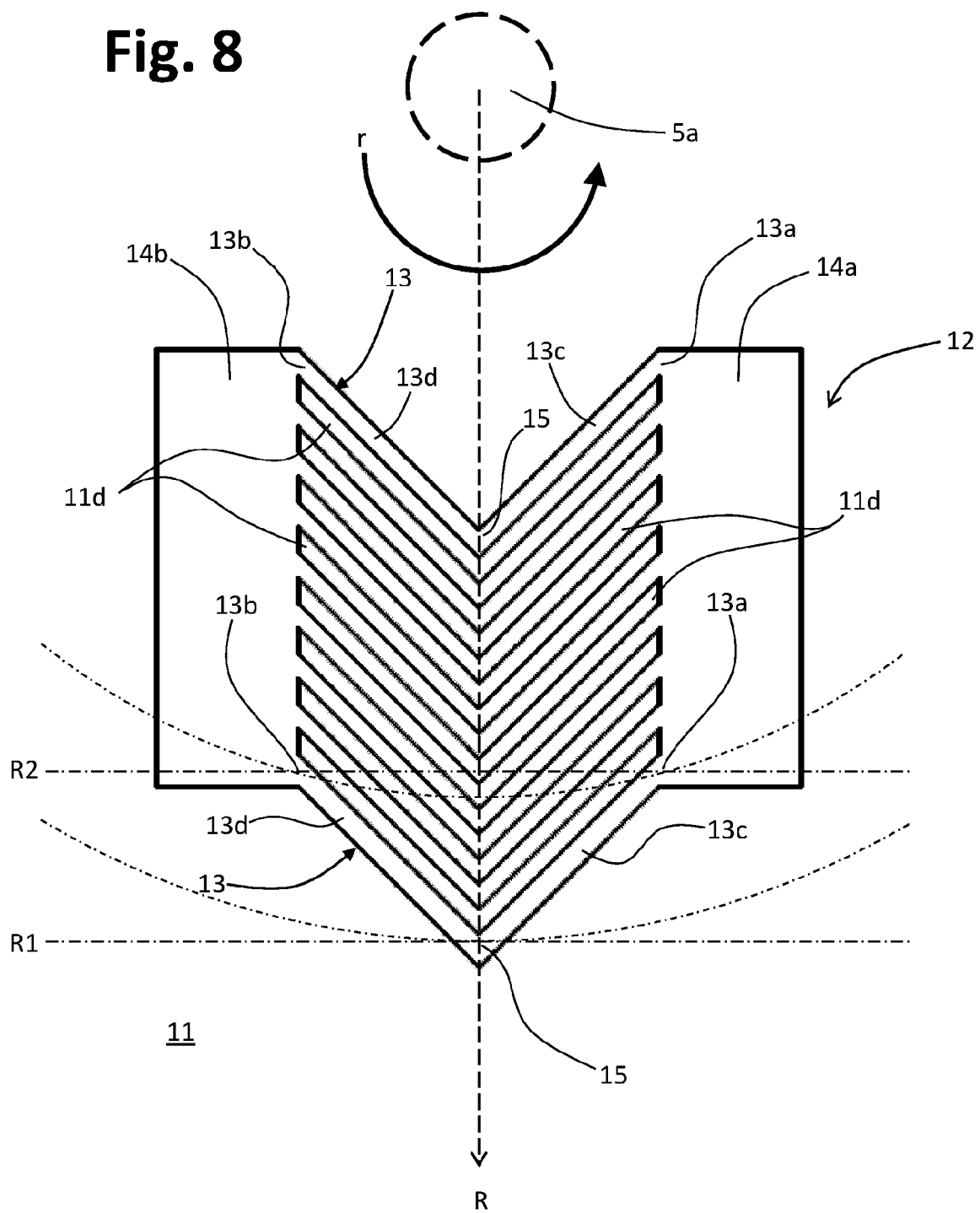
FIG. 8 is a schematic representation in front elevation of a microfluidic arrangement according to possible embodiments of the invention.

Once again with reference to FIG. 8, and according to an aspect of the invention, the at least one microchannel 13, or each microchannel, comprises, in a region intermediate between its ends 13a and 13b, at least one detection or accumulation area—designated by 15—that is at a distance R1, in a radial direction, from the centre of rotation of the substrate 11 that is greater than the distances R2, once again in a radial direction, of the two ends 13a and 13b of the microchannel from the same centre of rotation. In the schematic view of FIG. 8, provided by way of example, the centre of rotation is designated by 5a, assuming that the latter is represented by the member 5a of FIG. 1; the direction of rotation of the substrate is designated by r, whereas the radial direction is represented schematically by the arrow R. The area 15 is herein defined detection or accumulation area since in said area are designed to be concentrated particles possibly present in a volume of the fluid which penetrates into a microchannel 13, for purposes of a subsequent detection, in particular a detection aimed at the quantification and/or the identification and/or the study of the behaviour of said particles.

Preferably, the distance between the accumulation area 15 and the first end 13a is equal, or substantially equal, to the distance between the accumulation area 15 and the second end 13b; i.e., the area 15 is in a substantially central region of the microchannel 13. Therefore, the two microchannel branches 13c and 13d may have the same length.

Preferentially, the two ends 13a and 13b of the at least one microchannel 13, or of each microchannel, are substantially at one and the same second distance in a radial direction from the centre of rotation 5a of the substrate 11, even though this does not constitute an essential characteristic. For instance, from FIG. 8 it may be noted how the ends 13a and 13b of each microchannel 13 may be located substantially at the same distance R2 in a radial direction from the centre of rotation 5a. The ends 13a and 13b are preferentially located substantially at one and the same radial distance R2 from the centre of rotation 5a, in particular in order to prevent a fluid present within the microchannels 13 from possibly exiting therefrom in the course of centrifugation the device 10. It is preferable for the microchannels 13 to be open only at their ends.

Hence, thanks to the arrangement referred to above, any particles that may be contained in a volume of the fluid that penetrates into a microchannel 13 tend to concentrate in the accumulation area 15 as a result of the centrifugal force caused by a rotation of the substrate 11 about the centre of rotation 5a. For simplicity, the effect of the centrifugal force may be understood as being represented in FIG. 8 by the same arrow R that indicates the radial direction.

It is preferable for the accumulation areas 15 of the microchannels 13 to be without ways of exit for the liquid, so that, following upon centrifugation, the particles concentrate in any case in the liquid present at the aforesaid areas 15.

In various preferred embodiments, the microchannels 13 of one and the same microfluidic arrangement 12 are set at least in part substantially aligned or side by side in a radial direction R of the substrate 11, preferably close to one another. Indicatively, the walls or portions in relief 11d that separate the channels from one another may have a width of between 5 and 200 μm, preferably between 15 and 100 μm.

In various preferential embodiments, the chamber 14a and/or 14b has a depth equal or close to that of the microchannels 13, for example a depth of between 2 and 100 μm, preferably between 5 and 40 μm.

In preferred embodiments, the microchannels 13 of one and the same microfluidic arrangement 12 connect the two end chambers 14a and 14b, preferably with the latter that are located substantially at one and the same distance, in a radial direction, from the centre of rotation 5a of the substrate 11, in particular with a connection in parallel: in this case, the microchannels extend substantially in a position intermediate between the two chambers, with the latter that are substantially parallel to one another. Preferentially, the two chambers 14a, 14b are connected together only via the microchannels 13.

In various preferential embodiments, in the aforesaid accumulation area 15 the corresponding microchannel 13 is substantially V-shaped or U-shaped, or comprises two generally convergent stretches of microchannel, in particular two stretches of microchannel designed to form between them an angle or possibly radiused by a curved stretch: in the case so far exemplified, the area 15 is defined in the area of joining between the two branches 13c and 13d.

As it may be noticed from the figures, in various preferential embodiments, the microchannels 13 are substantially identical and arranged parallel to one another, along the whole length of the same, so as to assure a greater repeatability.

Figure 9:
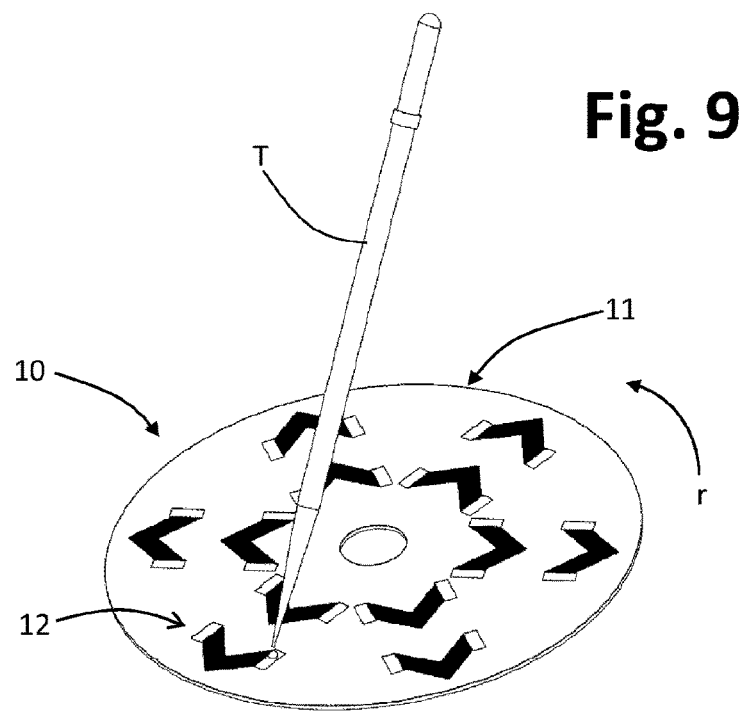
FIGS. 9 and 10 are schematic perspective views aimed at exemplifying a step of loading of a fluid sample into microfluidic arrangements according to possible embodiments of the invention.
Figure 10:
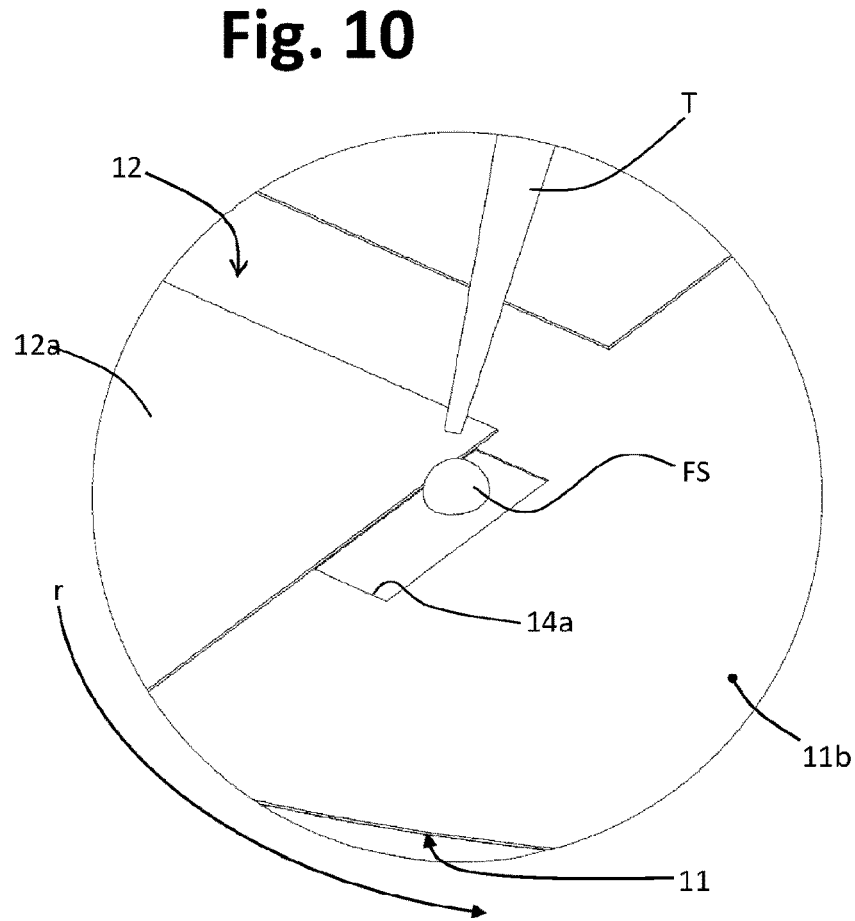

FIGS. 9 and 10 are a schematic illustration of a possible mode of introduction of a fluid sample in a microfluidic device according to possible embodiments of the invention. In the case exemplified, via a suitable tool T (such as a pipette designed to dispense a controlled amount of fluid, indicatively of the order of microlitres or of tens of microlitres) a sample FS of the fluid that is to undergo examination is deposited in at least one of the lateral chambers 14a or 14b of the microfluidic arrangement, preferably just one. The sample FS may be a simple drop of the fluid, as in the case exemplified, or may even have a larger volume, in any case in an amount sufficient to fill the microchannels 13.

The lateral chamber used facilitates introduction of the fluid sample into the microfluidic arrangement 12. Moreover, when this arrangement 12 includes a plurality of microchannels 13, as in the case exemplified, the lateral chamber used substantially functions as collector for introduction in parallel of the fluid into a number of microchannels. In other words, provision of at least one lateral chamber 14a and/or 14b, connected in parallel to which are the homologous ends of a number of microchannels 13, presents the advantage of avoiding the need to introduce individually respective fractions of the sample into the individual microchannels. It should be noted that, as mentioned previously, the chamber 14a, or each chamber 14a and 14b, could be obtained by a duct or a channel, via which the fluid sample is delivered to the inlet ends of the microchannel, or of each microchannel.

The possibility of connecting a number of microchannels to one and the same inlet—whether it is a chamber or a duct—makes it possible to increase the statistical basis of detection, i.e., to have available a number of repetitions of the same nominal conditions. In a preferential configuration the microchannels are grouped in at least two groups, each groups having at least one corresponding filling chamber 14a or 14b.

The number of microchannels to be used in the same nominal conditions will depend upon the type of use of the device and upon the volume of each microchannel: if, for example, the two opposite branches 13c and 13d of a microchannel 13 were each 1 cm long, with a width of 50 μm and a depth of 5 μm, the total volume would be $5 \cdot 10^6$ μm$^3$. With a concentration of 105 bacteria/mL, there would be 107 bacteria per cubic micrometre. This means that in each microchannel there would be on average 0.5 bacteria. This also means that, in the microchannels that contain at least one bacterium, the signal could double after a very short time (approximately 20-40 min) in the cases of proliferation, and remain constant in those in which there is no proliferation.

This type of use may be referred to as "digital antibiogram". Since the microchannels are very small and may be defined in positions very close together, with a similar pattern, it is possible to have, on a very limited area (such as that of a single microscope slide), a multitude of channels, for example between 250 and 500 microchannels.

At concentrations like the ones just referred to, it would be expedient to dedicate to each n-tuplicate (i.e., set of n microchannels used in the same nominal conditions) at the same nominal concentration a number of microchannels comprised between 100 and 200 in order to have a sufficient statistical basis. On a single centrifugable device, for example a disk-shaped one, it would hence be possible to test a multitude (various tens) of different conditions, each of which is n-tuplicated, where n is comprised between 100 and 200. For higher concentrations, it will, instead, be possible to group in a smaller number of channels the conditions that are nominally the same. For instance, in the case of concentrations of the order of one million bacteria per millilitre it is possible to use n-tuples of 10-20 microchannels for each nominally identical condition.

It is preferable for both of the ends 13a and 13b of each microchannel 13 to be open, in particular when set on top of the microchannels 13 is a covering element of the type designated previously by 12a (the fluid can thus penetrate from one end of the microchannel and the air contained in the latter can progressively be vented at the other end). In various embodiments, each microchannel 13 is filled by capillarity or by exploiting the hydrophilicity of at least one of the walls or surfaces that delimit the microchannel itself. On the other hand, in other embodiments (not represented), the fluid sample could be forced into the microchannels via a positive pressure or a negative pressure, for example using an over-pressure at inlet or a negative pressure at outlet (always with respect to ambient pressure).

Figure 11:
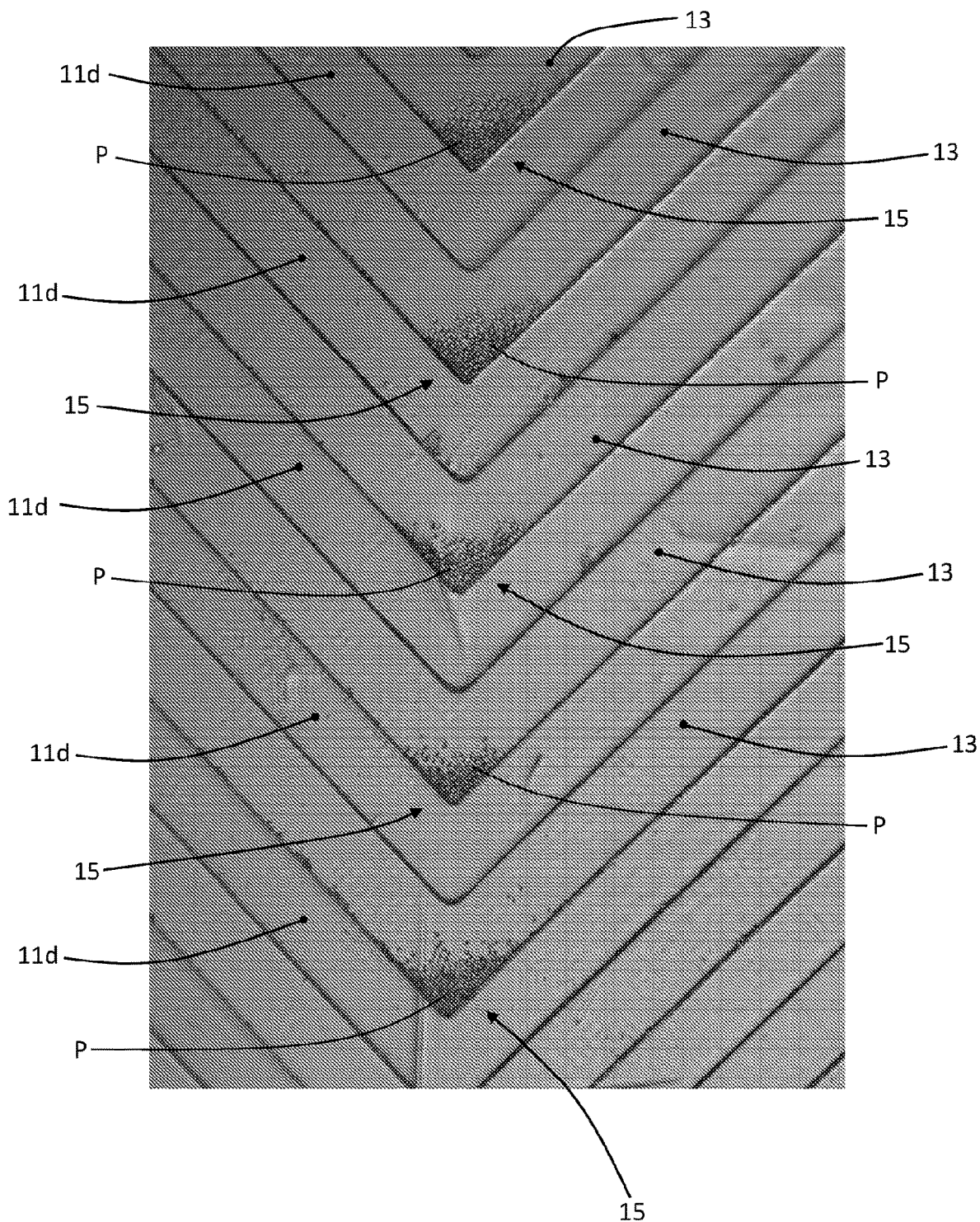
FIG. 11 is a macrophotograph aimed at illustrating the possible results of the use of a microfluidic device according to possible embodiments of the invention.

As already mentioned, following upon rotation of the device 10, and as a result of the centrifugal force, the particles present in the volume of liquid that occupies a microchannel 13 will tend to accumulate at the respective accumulation area 15, which is without ways of exit for the liquid. This is clearly visible in the macrophotograph of FIG. 11, from which it may be noted how, at at least some of the accumulation areas 15 respective masses of particles P are concentrated, within the liquid contained in the corresponding microchannels 13.

Of course, the dimensions of the microchannels 13 must be sufficient to enable inlet of the particles P of interest into them. In general terms, relatively shallow microchannels are preferable, i.e., ones having a height or depth of the order of the size of the particles of interest or just slightly greater. The reason for this is that—given the same number and size of the particles—in the area 15 of a shallow microchannel 13 the amounts of particles accumulated alongside one another will form an image in the plane having a larger area than a deeper microchannel, where the particles could lie on top of one another and thus falsify to a certain extent detection of the amount of particles and/or type thereof, if the concentrations are very low. The use of shallow microchannels, preferably with an approximately rectangular section, hence facilitates and improves the quality of reading of the amount and/or type using optical systems.

For instance, if a device 10 has to be used for separation of different types of cells in whole blood, it is preferable for there to have a height (depth) of the microchannels 13 of between 10 and 40 μm, preferably between 10 and 20 μm. If the object of analysis are, instead, bacteria, the microchannels may have a height (depth) of between 3 and 10 μm, preferably between 4 and 8 μm. Again, in the case where yeasts are to be measured, the height (depth) of the microchannels will preferably be between 5 and 20 µm, preferably between 8 and 12 µm.

Detection or reading can be carried out by quantifying in an optical way the size of the mass of particles that, as a result of centrifugation, is formed at each accumulation area 15. It is also possible to carry out such a detection of the amount and/or type by measuring the intensity of fluorescence, in the case where the particles have previously been marked with fluorochromes.

Figure 12:
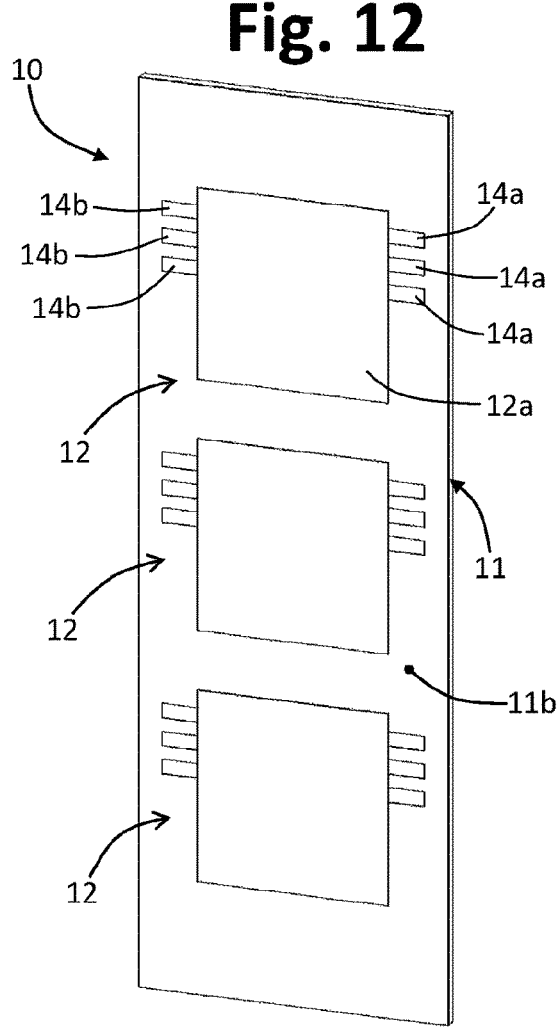
FIGS. 12, 13, 14, and 15 are views similar to those of FIGS. 3, 4, 5, and 6, respectively, regarding further microfluidic devices and arrangements according to possible embodiments of the invention.
Figure 13:
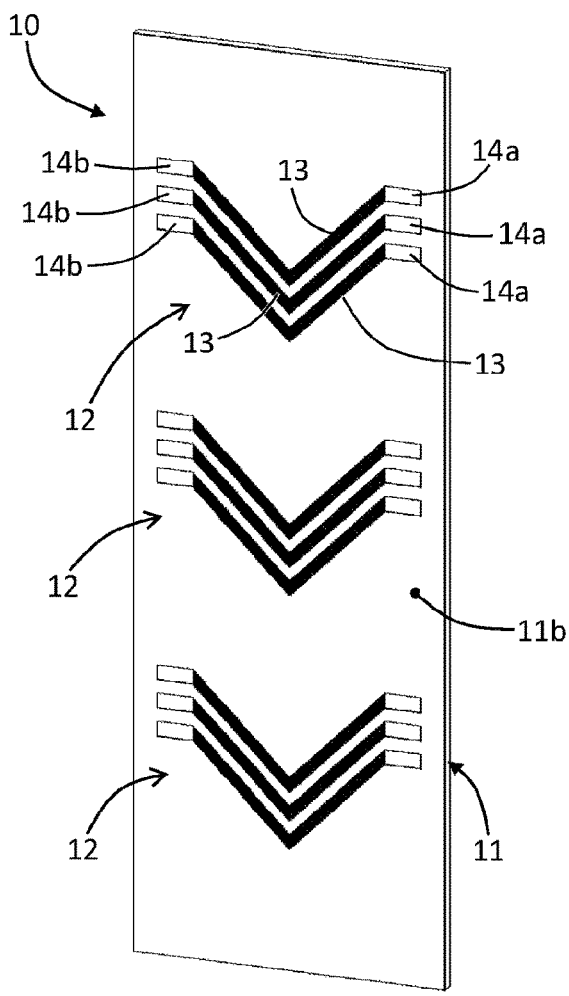
Figure 14:
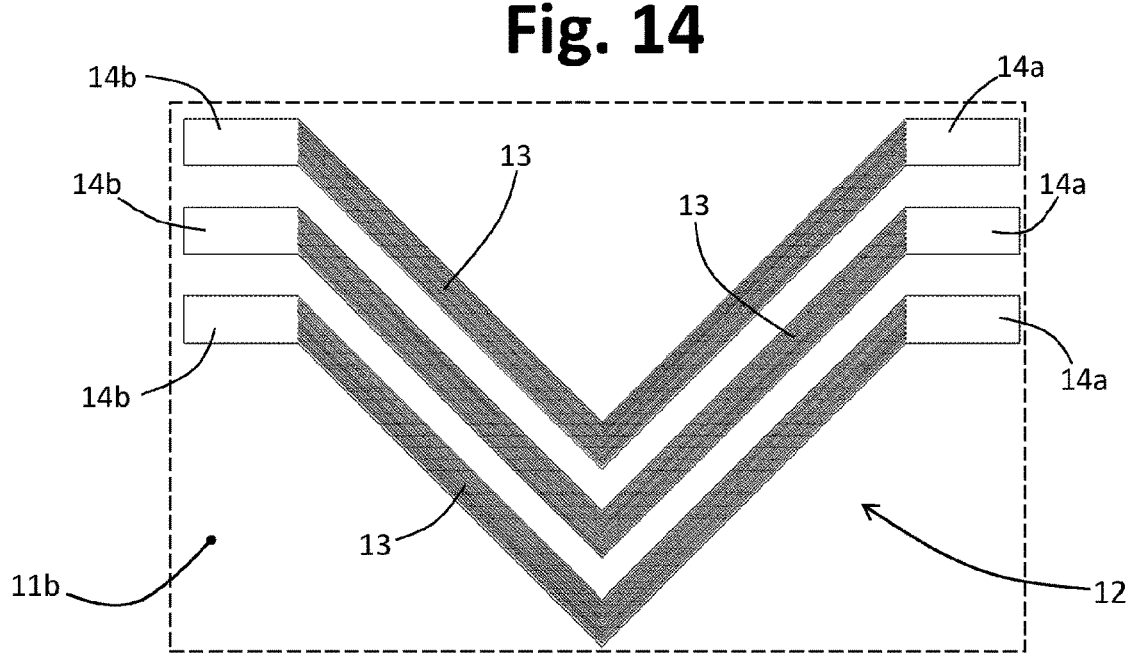
Figure 15:
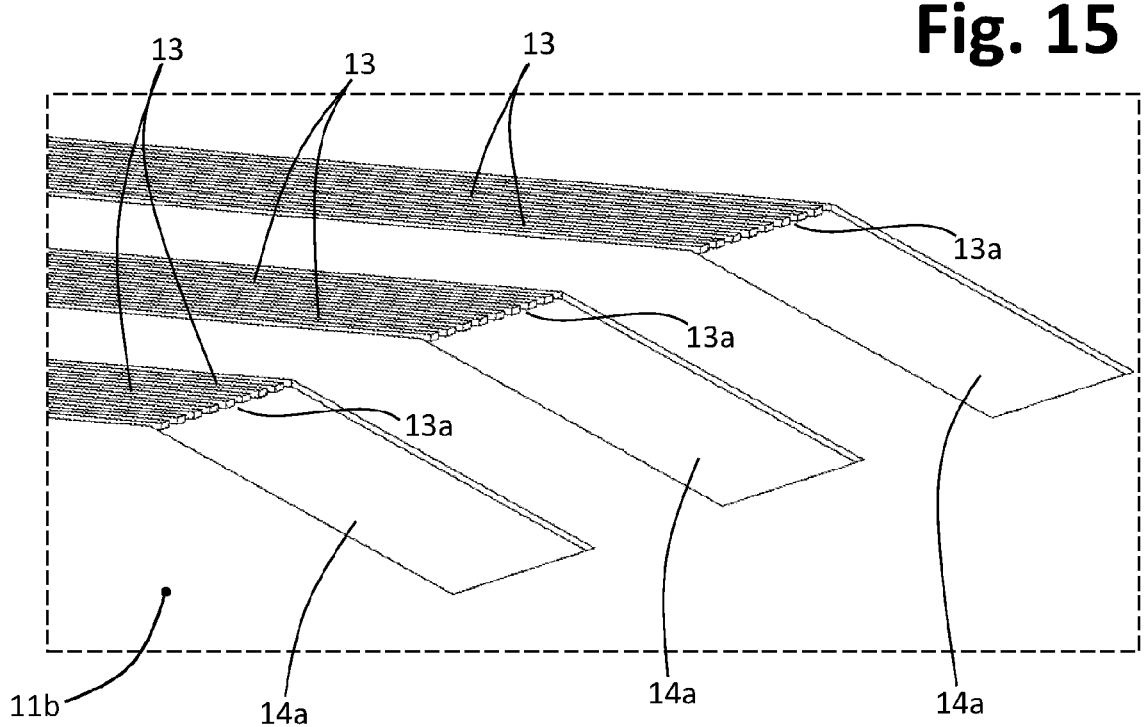

FIGS. 12 and 13 illustrate, with views similar to those of FIGS. 3 and 4, possible variant embodiments of a quadrangular centrifugation support 10 (or of a quadrangular portion of a centrifugation support 10 shaped like a disk or having a different shape). In embodiments of this sort, each microfluidic arrangement 12 comprises a number of sets of microchannels 13, set at a slight distance apart in a radial direction, which are connected to respective lateral chambers 14*a* and 14*b*; in the example illustrated, and as is clearly visible also in FIGS. 14 and 15, provided for each microfluidic arrangement 12 are three sets of microchannels 13, and hence three lateral chambers 14*a* and three lateral chambers 14*b*. The operating principle of the microfluidic device is similar to the one just described.

The fact that, in embodiments of this sort, each microfluidic arrangement 12 envisages a plurality of sets of microchannels 13 separate from one another, preferably with each plurality associated to at least one respective lateral chamber 14*a* and/or 14*b*, may prove useful for the purposes of analysis, in particular both to have available different conditions of detection simultaneously (and hence parallelisation) and to increase the statistical basis if it is chosen to use a number of sets in the same nominal conditions.

In various embodiments, the microchannels of the arrangements 12 are used only for the detection of particles of interest contained in the fluid sample, whereas, in other embodiments, the microchannels can be exploited also as culture wells, in particular in the case where the particles that are to be detected are micro-organisms capable of reproduction. Alternatively, some microchannels may be "loaded" with biological materials (for example, bacteria) that outside the device have been induced to proliferate or have been inhibited by antibiotics.

Figure 16:
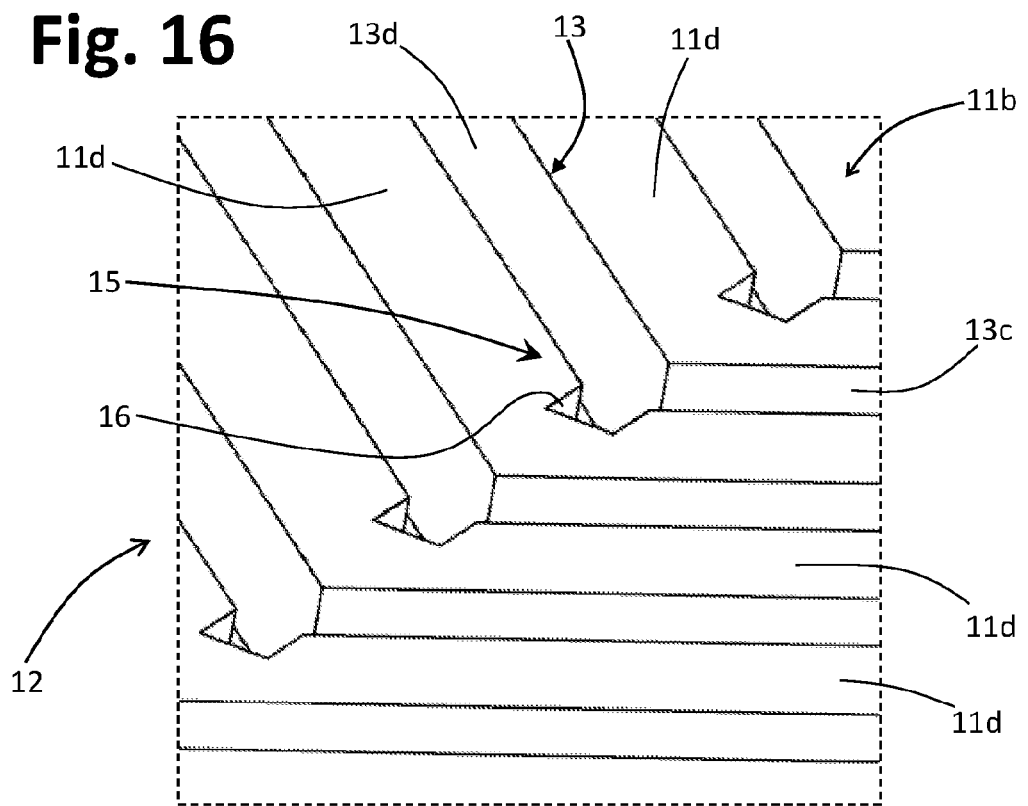
FIG. 16 is a schematic perspective view of a portion of a microfluidic arrangement according to possible embodiments of the invention.

Represented schematically in FIG. 16 is an intermediate portion of a microfluidic arrangement 12, at the accumulation areas 15 of the microchannels 13. As may be noted, in various embodiments, this area 15, preferably at the intersection between the microchannel branches 13*c* and 13*d*, may be shaped so as to define at least one recess or cavity, which forms substantially a well 16, which can be used as a culture well. The possibility of using at least part of the microchannels 13 also as culture wells proves particularly advantageous when the fluid being analysed is a culture broth or the arrangement 12 contains a culture medium. In this perspective, the microfluidic devices according to the invention are particularly advantageous for the purposes of execution of antibiograms, in particular fast antibiograms, as also explained hereinafter.

Figure 17:
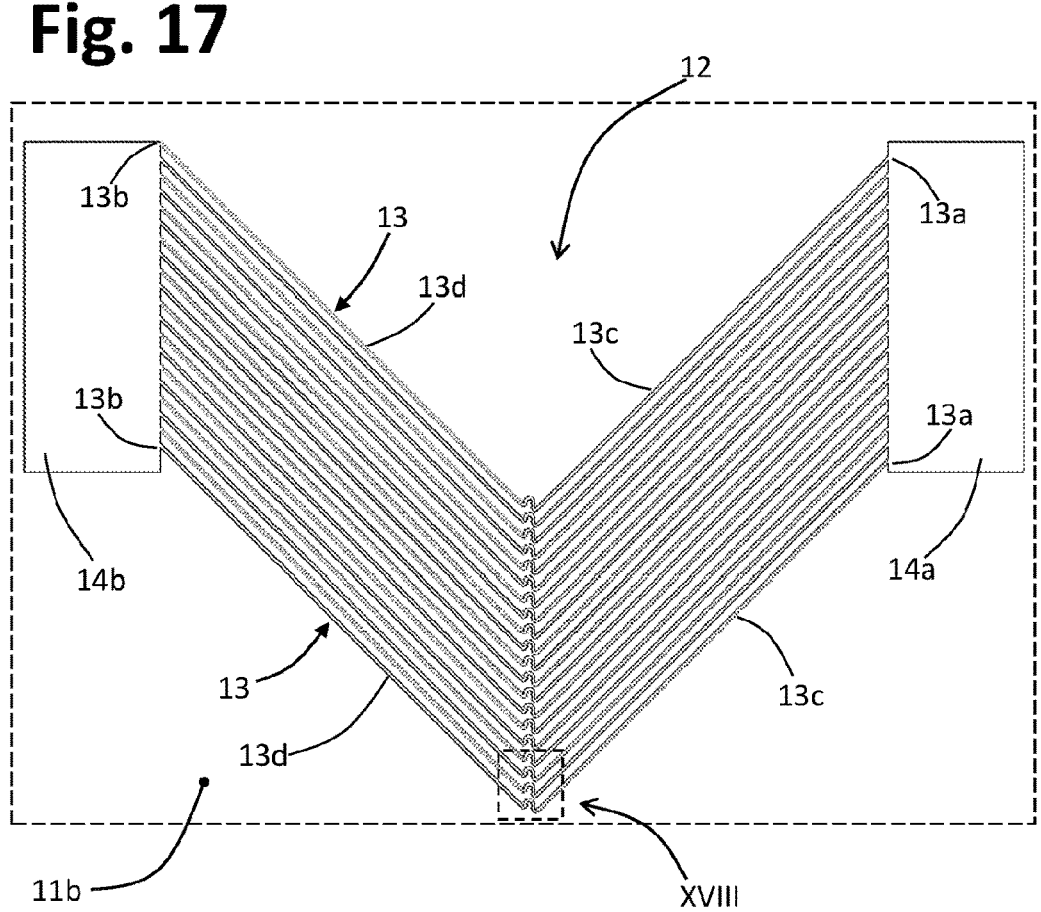
FIGS. 17 and 18 are a schematic view in front elevation and a corresponding detail at a larger scale, respectively, of a microfluidic arrangement according to possible embodiments of the invention.
Figure 18:
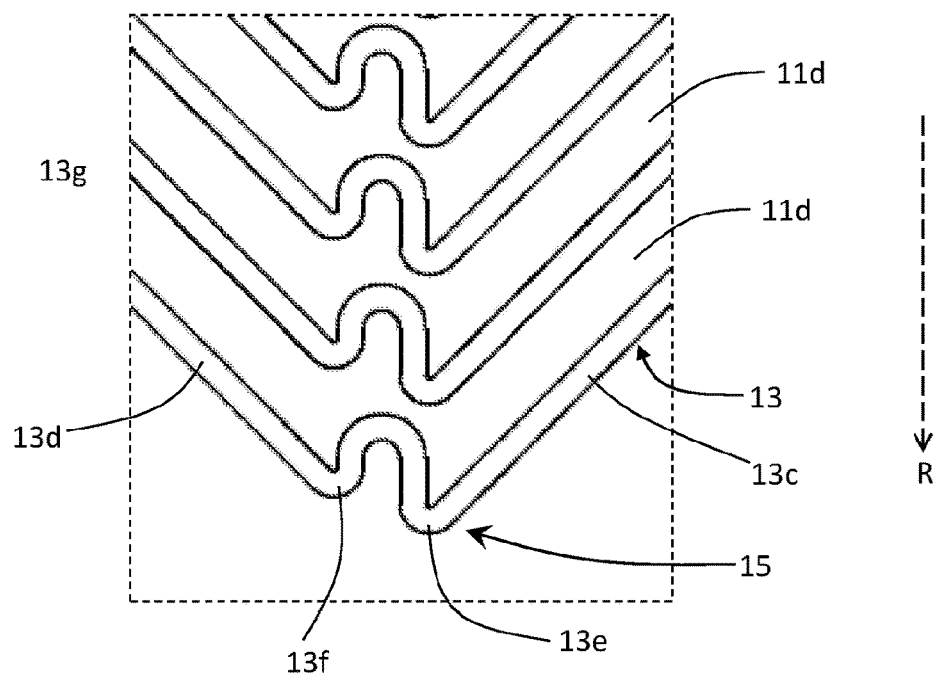

In various embodiments, the at least one microchannel 13, or each microchannel, of a microfluidic arrangement 12 may include at least one syphon. An embodiment of this sort is exemplified in FIGS. 17 and 18.

In various embodiments of this sort, in the area 15, the two microchannel branches 13*c* and 13*d* may be connected together by two opposite syphons 13*e* and 13*f* (i.e., a double syphon), which basically form two accumulation sub-areas, one for each branch 13*c* and 13*d*, respectively. The presence of these two sub-areas may prove useful for verifying possible differences of concentration of particles between the two branches 13*c* and 13*d*, due to different components of the centrifugal force (for example, in the case of microchannels with substantially specular V-shaped branches connected via a double syphon) and/or to the incidence of different shapes or lengths of the two convergent branches of the microchannel (for example, one branch vertical and the other inclined), where the friction and/or the adhesion between the particles and the walls of the microchannel could affect the analysis.

Figure 19:
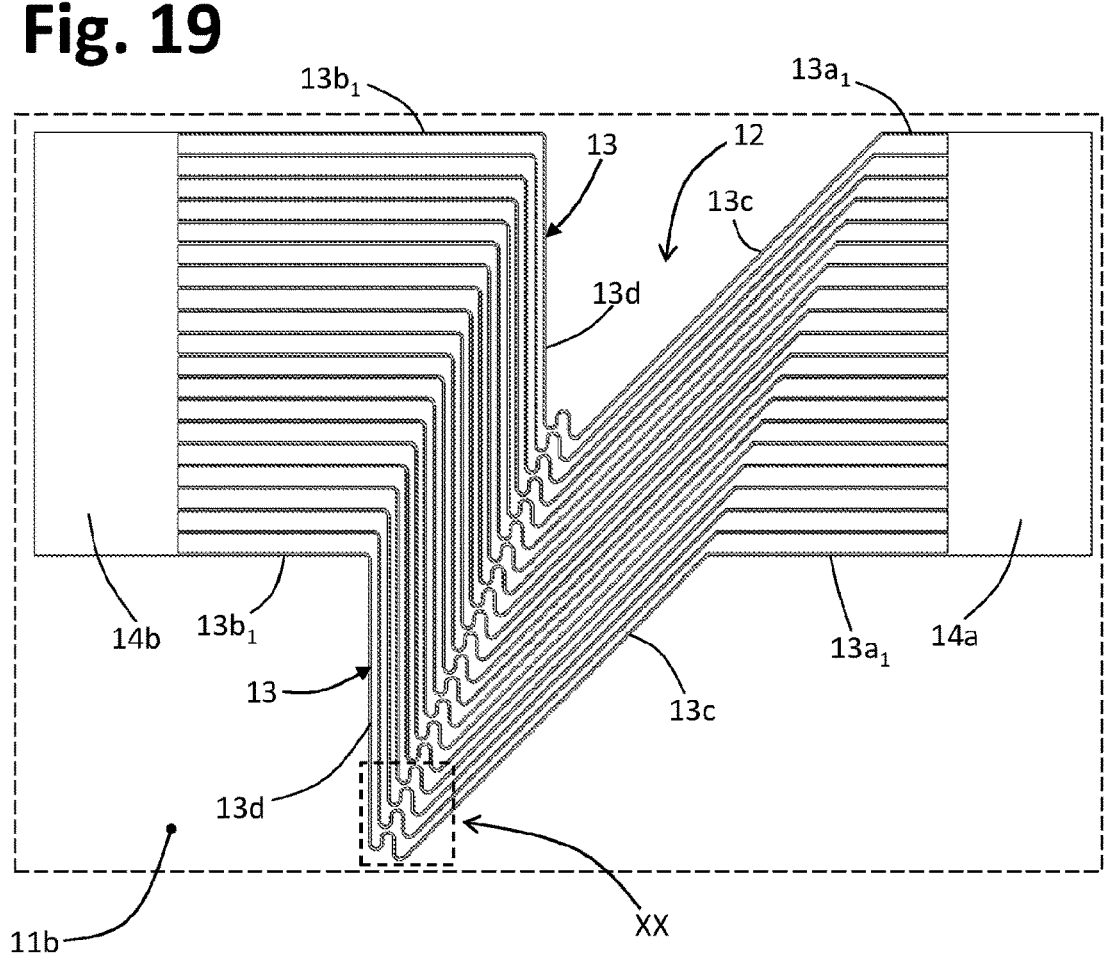
FIGS. 19 and 20 are a schematic view in front elevation and a corresponding detail at a larger scale, respectively, of a microfluidic arrangement according to possible embodiments of the invention.
Figure 20:
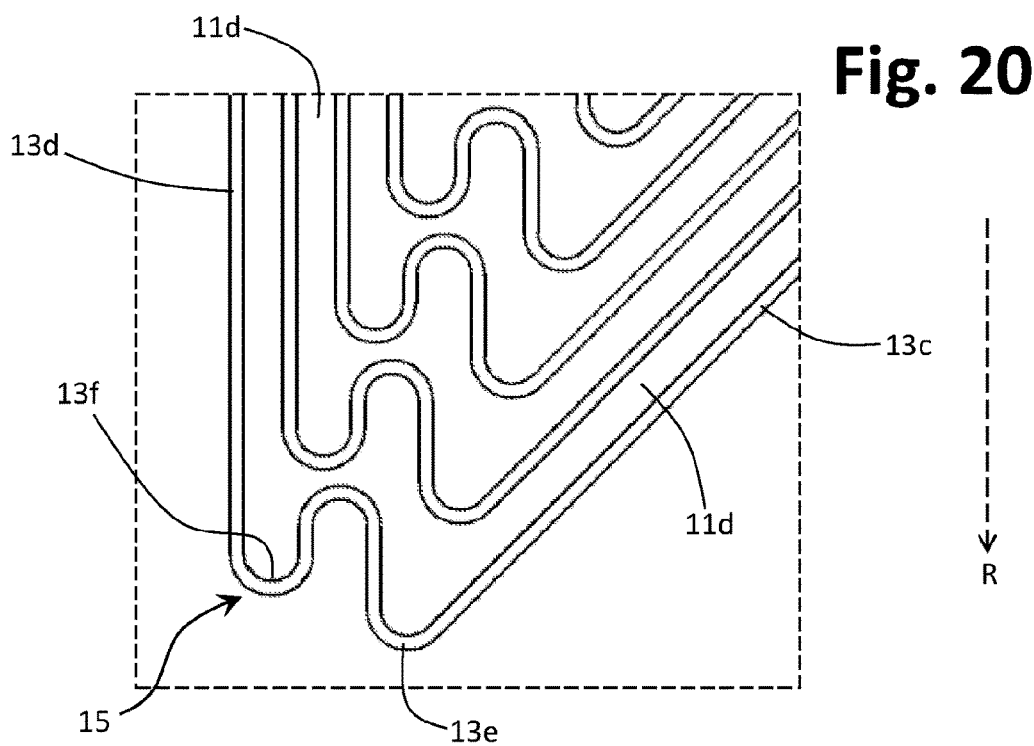

With particular reference to the latter case, FIGS. 19-20 exemplify embodiments in which each microchannel 13 comprises respective end portions 13*a*1 and 13*b*1 that extend substantially perpendicular to the radial direction R, and branching off from which are the generally convergent branches 13*c*, 13*d*, which define between them the accumulation areas 15. In the example, the branch 13*d* extends substantially in the radial direction R. and the oblique branch 13*c* is connected to the lowest point of the branch 13*d* by means of two opposed syphons 13*e* and 13*f* (or a double syphon), where preferably the syphon 13*e* has the function of blocking the particles that come from the oblique portion 13*c* and the syphon 13*f* operates as accumulation area.

This solution is preferable in the case of particles that tend to adhere to the walls of the microchannel 13. The vertical branch 13*d* minimises this effect in so far as, during centrifugation, the particles undergo an acceleration substantially parallel to the walls of the branch 13*d*. On the other hand, the particles that are located in the fluid contained in the oblique branch 13*c* will have a component of acceleration tending to push them towards a wall of the branch 13*c*. Adhesion of particles to the walls of the microchannel causes the loss of at least some of these particles in the count: the syphon 13*e* prevents that part of particles that does not adhere to the walls of the oblique branch 13*c* from reaching the area of detection for the purposes of the count—here represented by the syphon 13*f*—and from possibly vitiating the detection owing to the variability of the amounts arriving.

Consequently, in various embodiments and irrespective of the possible presence of one or more syphons, at least one part of a microchannel branch that leads to a respective accumulation area extends substantially in a radial direction, in particular in order to minimise the risks of adhesion of particles.

Figure 21:
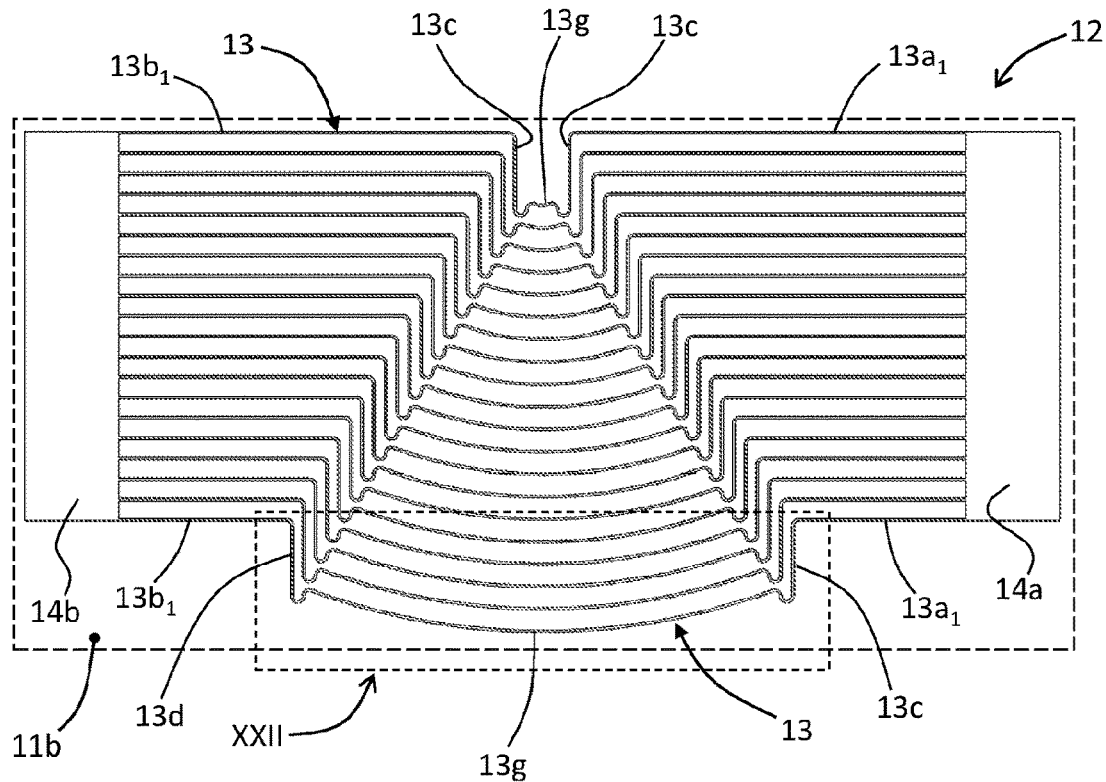
FIGS. 21 and 22 are a schematic view in front elevation and a corresponding detail at a larger scale, respectively, of a microfluidic arrangement according to possible embodiments of the invention.
Figure 22:
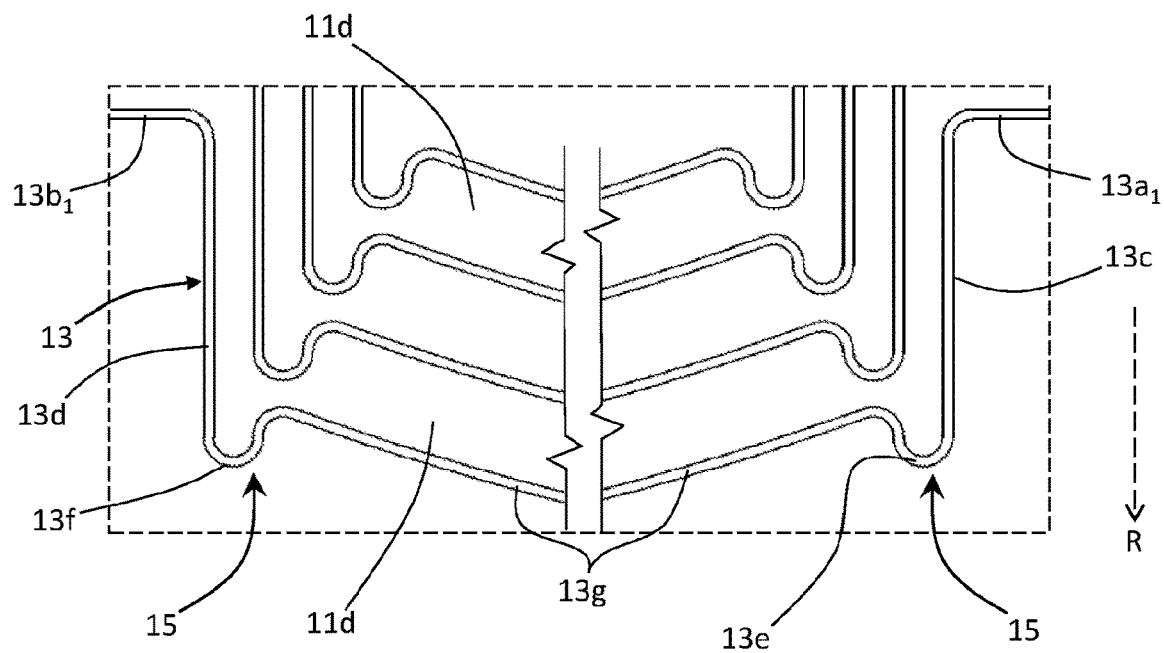

Exemplified in FIGS. 21 and 22 are embodiments in which each microchannel 13 defines two distinct accumulation areas 15 in positions set at a distance or remote from one another. Also in this case each microchannel 13 comprises respective end portions 13*a*1 and 13*b*1 that extend substantially perpendicular to the radial direction R, and branching off from which are the branches 13*c*, 13*d*, which here are set substantially in the radial direction R. As has been said, such an arrangement minimises the risks of adhesion of particles to walls of the microchannel, and hence maximises the concentration of particles in the accumulation areas.

Provided in the lower points of the branches 13*c* and 13*d* are the two opposed syphons 13*e* and 13*f*, respectively, which form respective accumulation areas of the microchannel 13 considered. The two syphons 13*e* and 13*f*, i.e., the two areas 15, are located substantially at the same radial distance from the centre of rotation of the microfluidic device and are connected together by means of an intermediate stretch 13 g of the microchannel, here generally curved (concave) in the radial direction.

The presence of the two accumulation areas 15 constituted by the syphons 13e and 13f makes it possible to have available two distinct detection areas, for example to increase (double) the statistical basis given the same number of microchannels 13 used.

As already indicated, the microchannels of a plurality have to be preferably identical to each other, while their opposite branches (right and left) may be even different from each other.

In various embodiments, to at least one microchannel, or to each microchannel, there can be associated at least two electrodes, in particular at least in a respective accumulation area 15, or in a position of the microchannel that is between an end thereof and an accumulation area thereof. These electrodes may be electrodes for detection or else manipulation electrodes of the particles.

For instance, in various embodiments, at least one pair of electrodes at an accumulation area 15 may be used to carry out a reading of amounts of particles via detection of an electrical impedance. It is also possible to carry out differential readings by positioning further pairs of electrodes in portions of the microchannel comprised between a corresponding end 13a, 13b and an area 15, in order to make it possible to distinguish the contribution to the electrical impedance represented by the particles from the contribution represented by the fluid of the sample. In the cases where the fluid sample is a culture medium or a physiological solution, the electrical conductivity is relatively high on account of the ions dissolved in the fluid.

Pairs of electrodes in the upper part of the microchannels (i.e., in a position closer to the corresponding ends than to an accumulation area) also enable verification of whether the microchannel is filled properly with the fluid containing the particles to be counted (this verification is relatively easy, considering that the fluid has in general a conductivity much higher than that of air, which is an insulator).

Figure 23:
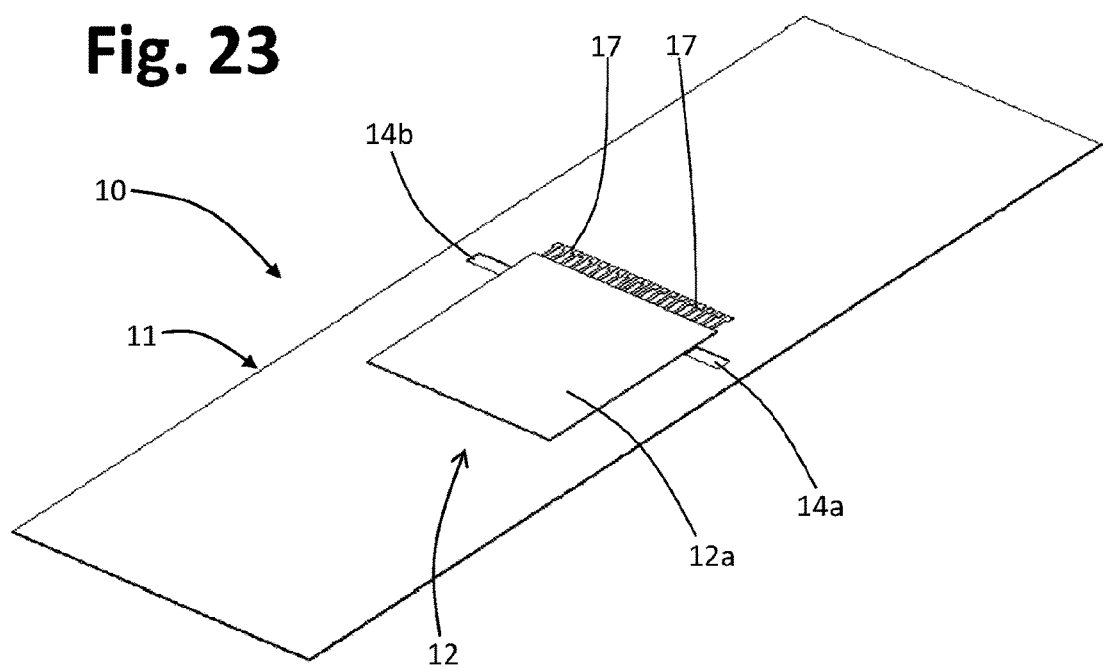
FIG. 23 is a schematic perspective view of a microfluidic device according to possible embodiments of the invention.
Figure 24:
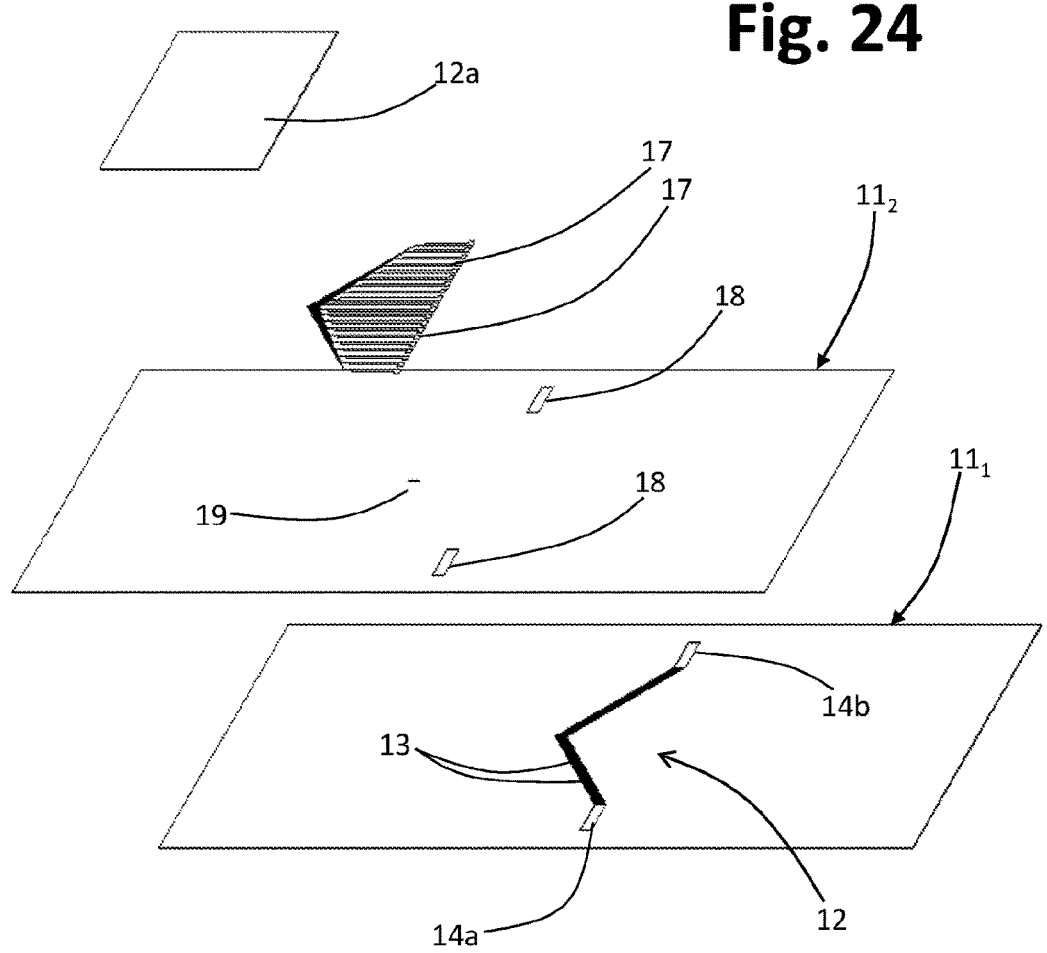
FIG. 24 is an exploded schematic view of the device of FIG. 23.
Figure 25:
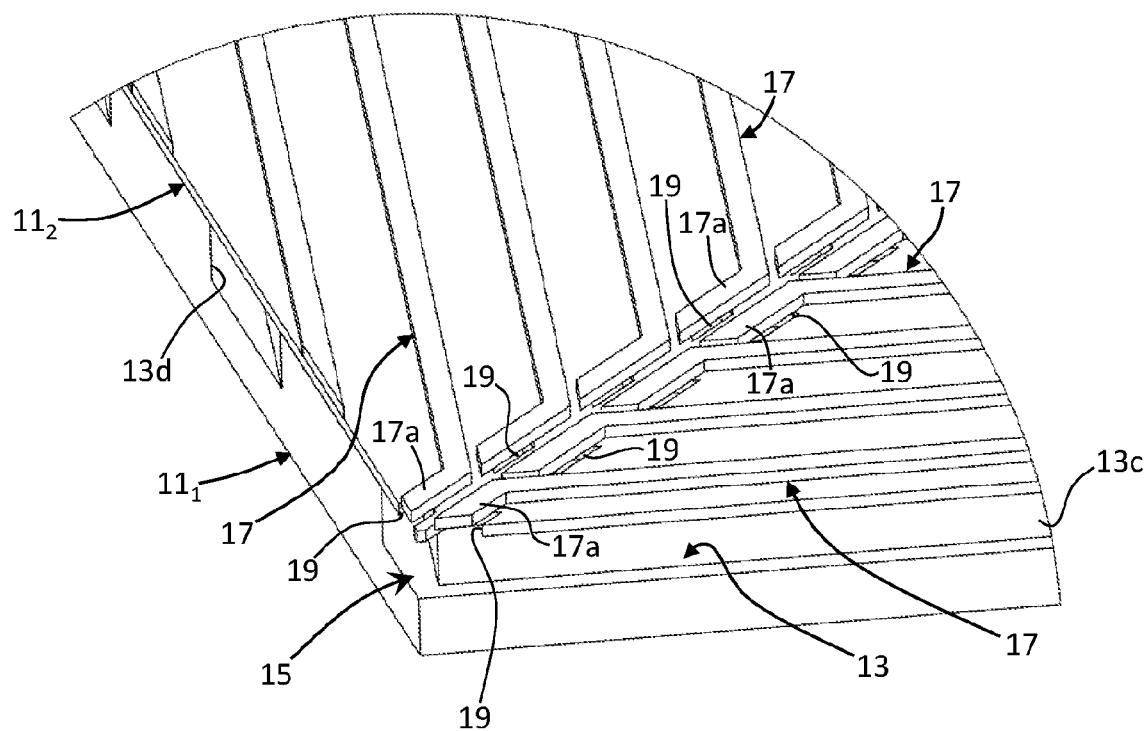
FIG. 25 is a sectioned perspective view of a portion of a device of the type illustrated in FIG. 23.

FIGS. 23-25 are schematic illustrations of a quadrangular device 10 (or a quadrangular portion of a device 10 shaped like a disk or having a different shape) with microchannels 13 provided with electrodes 17 in respective accumulation areas.

As may be noted from FIG. 24, in various embodiments, the device 10, i.e., the substrate 11, may be formed by a number of layers set on top of one another. Provided in the example is a lower layer $11_1$, for example made of one of the electrically insulating materials previously mentioned for the substrate, defined in which is at least one microfluidic arrangement 12, i.e., the corresponding microchannels 13 with the corresponding chambers 14a and/or 14b. An upper layer $11_2$ is then provided, made of electrically insulating material, preferably transparent, for example a polymer, which is provided with windows or openings 18 in positions corresponding to the chambers 14a and 14b of the layer $11_1$, as well as with a series of micro-openings or micro-windows 19 in positions corresponding to the accumulation areas 15 of the various microchannels 13 of the layer $11_1$. Set on the electrically insulating layer $11_2$ are the pairs of electrodes 17, here in a position intermediate between the two windows 18, with the electrodes 17 that are shaped so as to have respective detection ends at the accumulation areas 15 of the microchannels 13.

This may be seen, for example, in FIG. 25, where designated by 19 are some of the aforesaid micro-openings and designated by 17a are the detection ends of the various electrodes 17. As may be noted, basically at each accumulation area, defined on the layer $11_2$ are two generally parallel micro-openings 19, each of which is set on top of the detection end 17a of a corresponding electrode 17: in this way, a part of these detection ends 17a faces the inside of the microchannel 13, for the necessary detection of an electrical type (impedance, or resistivity, or conductivity, etc.).

To return to FIGS. 23-24, in various embodiments, the electrodes 17 are at least in part protected at the top by a corresponding covering element 12a, which is also made of electrically insulating and preferably transparent material. In various embodiments, at least one portion of the electrodes 17 is, however, exposed, as for example may be seen in FIG. 23, for the purposes of electrical connection to a system that manages the use of the electrodes 17. In various embodiments, the aforesaid electrical connection is obtained via sliding contacts provided on the centrifugation and/or detection device 1, which are configured for contacting the aforesaid exposed part of the electrodes 17. In the case where the measurement occurs in static conditions, for example at the start and end of centrifugation, the contacts may, for example, be constituted by spring contacts or other types of contact connections.

Preferably, also the electrodes 17 are made at least in part of an electrically conductive transparent material.

Given that the device 10 according to the invention can be used for accumulating cells in a precise position (i.e., at the areas 15), electrodes of the type referred to may be used also for carrying out manipulations on the cells themselves, for example electroporation, or else for keeping them in position, for example by means of dielectrophoresis.

As mentioned previously, in various embodiments, detection of the particles that accumulate in an area 15 of a microchannel 13 is carried out in an optical way.

For this purpose, in various embodiments, the centrifugation device 1 itself can integrate optical sensor means. The sensor means may include a single sensor, which moves between various points to be detected, or else an array of sensors (for example, as in an optical scanner). In general, then, one and the same device 1 can integrate functions of centrifugation and functions of detection or reading, in particular by exploiting rotation of the device 10 both for the aforesaid centrifugation and for the reading operation using the sensor means.

Figure 26:
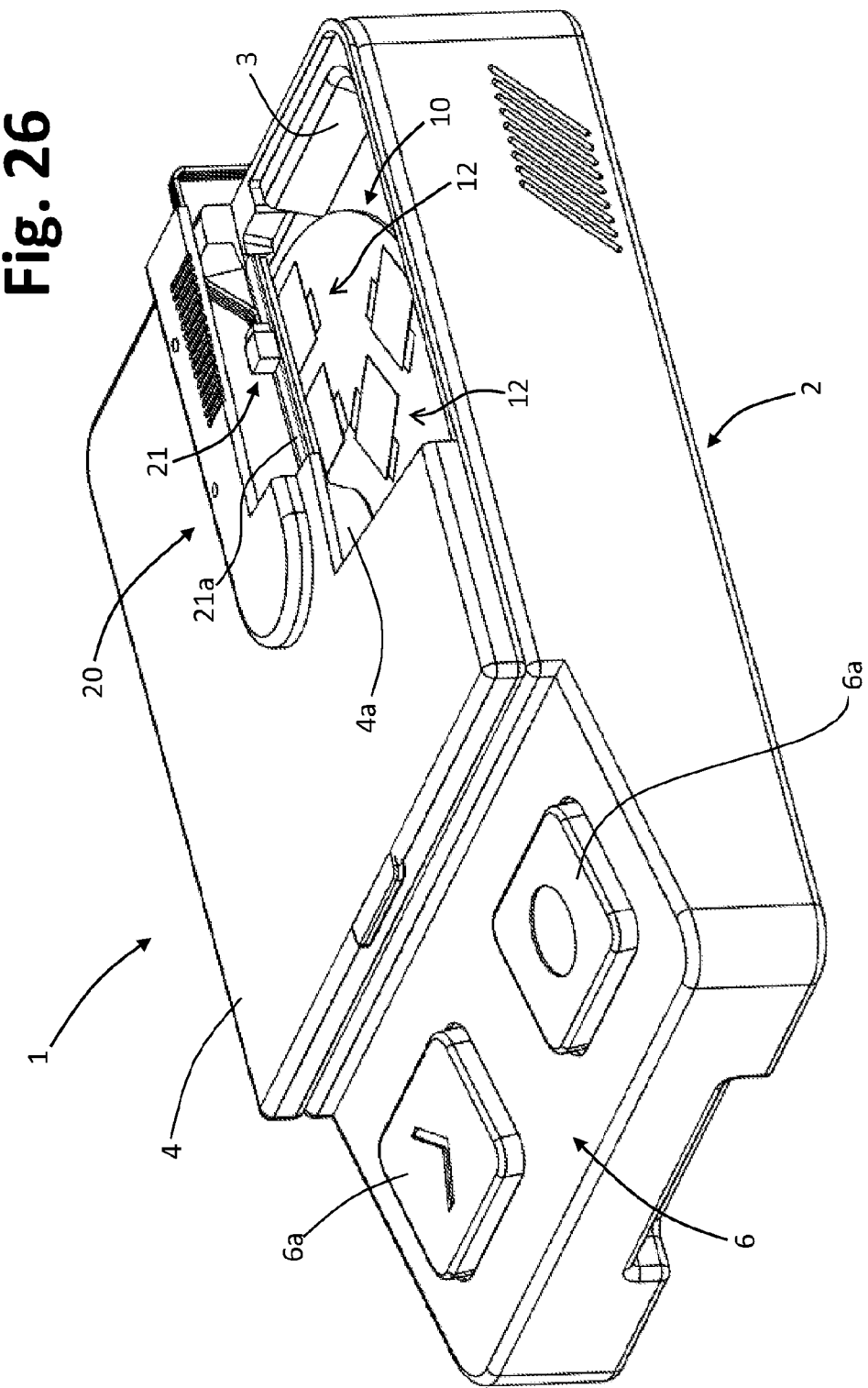
FIGS. 26 and 27 are schematic perspective views of centrifugation and/or detection devices according to possible embodiments of the invention.

For instance, FIG. 26 exemplifies a centrifugation device 1 having a detection or reading unit 20—here associated to the lid 4—that includes a single optical sensor 21 (which may, on the other hand, itself be constituted by an array of optical sensors). The sensor 21 is mounted movable, for example via an actuator of its own not mentioned, on a corresponding guide 21a that may be made of transparent material or that is in any case shaped so as not to constitute a hindrance to acquisition of images. In the case exemplified, the detection unit represented by the sensor 21 can be displaced in the radial direction relative to the device 10 so as to carry out the necessary optical detections on a number of microfluidic arrangements 12 aligned on the device 10 in the aforesaid radial direction. Of course, given that the device 10 can be set in rotation by the device 1, via the sensor 21 it is possible to carry out optical detection also on a number of microfluidic arrangements 12 set side by side or arranged on the device 10 along a circumference.

The control system of the device 1 may, on the other hand, be pre-arranged for controlling the position in the radial direction of the sensor 21 according to the optical detections to be carried out each time. This control system may also be pre-arranged so as to carry out optical detections after the end of the centrifugation step, by driving and stopping each time the device 10 in the various angular reading positions, or else so that the optical detections are performed with the device 10 moving, preferably at low speed, such as a speed during detection or reading lower than the centrifugation speed, i.e., by synchronising rotation with reading.

In various embodiments of the invention, the optical sensor means 21 of a centrifugation and/or detection device of the type referred to are configured for acquiring a cumulative optical signal or a cumulative image of a plurality of accumulation regions of the micro-fluidic device, i.e., a signal or image regarding all the accumulation areas 15 of the microchannels 13 of a corresponding microfluidic arrangement 12. The centrifugation and/or detection device is then pre-arranged, for example via suitable software, for processing, on the basis of the aforesaid optical signal or image, information representing an amount of particles that have accumulated in each of the individual accumulation areas 15 of the various microchannels of one and the same microfluidic arrangement, in particular with a processing that enables estimation of the number of particles for each individual microchannel 13.

In other embodiments, for example when the optical sensor 21 includes an array of sensors, such as in an optical scanner, the sensor itself may be configured for acquiring an individual optical signal or an individual image of the accumulation area 15 of each individual microchannel 13 of a corresponding microfluidic arrangement 12. Also in this case, the centrifugation and/or detection device is pre-arranged for processing, on the basis of the aforesaid optical signal or image, information representing an amount of particles that have accumulated in each of the individual accumulation regions 15 of the various microchannels of the microfluidic arrangement.

Of course, a device 1 may also be devised so as to be able to employ both of the techniques of optical detection (i.e., collective and individual) referred to.

Figure 27:
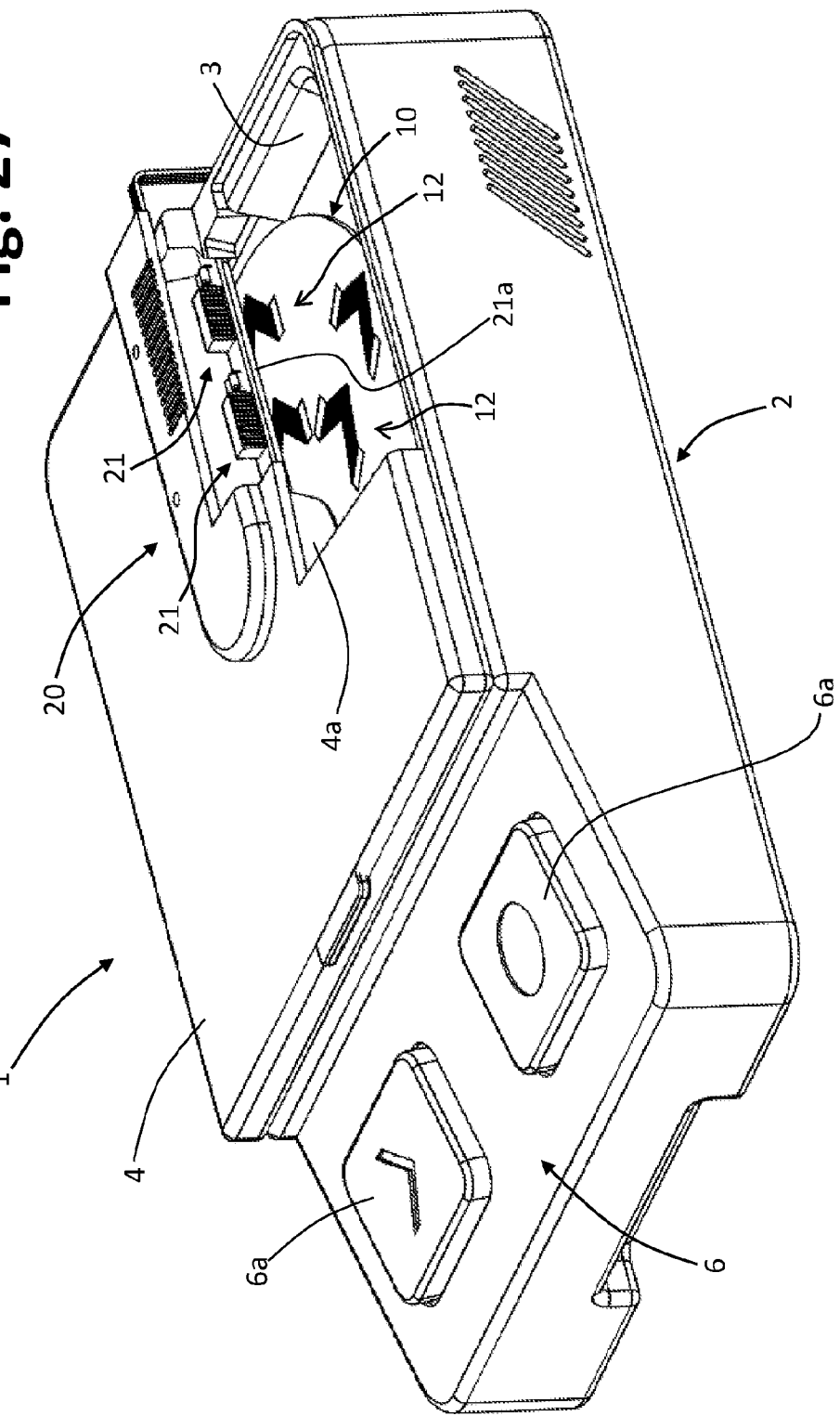

FIG. 27 represents the case of a device 1, the detection or reading unit 20 of which includes two stationary optical sensors 21, for example each formed by an array of optical sensors, which are set in such a way that, in the course of a movement of rotation of the device 10, at least the accumulation areas 15 of the corresponding micro-fluidic arrangement 12 are cyclically located underneath the sensors themselves, for the necessary optical detections. Since the substrate of the device 10 is preferably made of transparent material, optical configurations will be possible that operate both in transmission and in reflection, or that measure scattering of the particles in different directions.

As already mentioned, a microfluidic device 10 according to the invention can be used for the purposes of simple counting and/or detection of the type of the particles contained in the fluid sample, or also for more complex functions of analysis, for example for execution of antibiograms (in which case the microchannels could also be pre-treated, for instance by introducing antibiotics therein).

The supports or microfluidic devices and the centrifugation and/or detection devices according to the invention may advantageously be used for the purposes of evaluation of the capacity of proliferation of bacteria and microbes and, subordinately, for the purposes of determining a profile of susceptibility thereof to antibiotics (antibiogram) in short times and with small volumes of the fluid sample.

The methodologies known for this purpose are based upon evaluation of the capacity of a microbe or of a bacterium to form colonies in a medium suited to its growth, or upon evaluation of the turbidity of a culture broth following upon proliferation of the microbe. The capacity of an antibiotic to inhibit proliferation of a microbe or of a bacterium is evaluated classically by counting the corresponding colonies or on the level of turbidity of the corresponding culture broth, which are characteristics that vary as a function of the susceptibility of the microbe or bacterium to antibiotics.

This susceptibility is linked to the capacity of the antibiotic to inhibit efficient proliferation of a bacterial strain, and it is evident that the times linked to this type of analysis depend upon the rate at which the microbe or bacterium proliferates. The approach followed according to the prior art is essentially based upon the fact that a "two-dimensional" layer of bacteria or microbes (a colony) can grow until it becomes visible to the naked eye, or upon the fact that proliferation of the bacteria or microbes in a liquid can be such as to modify, in a statistically significant way, the turbidity of the liquid itself, this turbidity being measurable by means of photometry in the turbidity range (the reading is typically made at a wavelength of between 500 and 600 nm).

The techniques proposed herein, which exploit the microfluidic devices described previously, are based, instead, upon some parameters that do not consider either the two-dimensional growth of the layer of bacteria or microbes or the growth in the liquid, which is read as increase in turbidity.

More in particular, the methodologies proposed herein envisage:
i) obtaining a short-term growth of the biological material (for example, urines directly collected by the patient), with or without the addition of growth factors (for example, bacterial culture broth, such as BH);
ii) introducing the culture obtained in the previous step into the microchannels 13, which are seeded with the same concentration of biological material and/or culture medium (for this purpose, it may be particularly advantageous to provide, in the microchannels 13, wells like the ones designated by 16 in FIG. 16);
iii) measuring the proliferation of the bacteria in the microchannels 13;
iv) identifying one or more "negative" microchannels 13, i.e., ones in which only the culture medium will be added (for example, at 50% with PBS buffer or physiological solution);
v) identifying one or more "positive" microchannels 13, i.e., ones capable of verifying the proliferation capacity of the bacterial or microbial strain present in the system of microchannels 13; and
vi) identifying a series of microchannels 13, containing the antibiotic, in such a way as to verify the resistance or susceptibility of the bacterial or microbial strain present in the seeded biological material to antibiotics.

The measurement of susceptibility to antibiotics may be carried out using different strategies, starting from sedimentation of the bacteria or microbes after proliferation in the accumulation areas 15 of the microchannels 13, which can be obtained, as has been said, via centrifugation of a device 10. This approach advantageously makes it possible to carry out the necessary comparisons between:
the amounts of bacteria or microbes present in the starting material;
the amounts of bacteria or microbes present at the end of incubation; and
the amounts of bacteria or microbes present in the microchannels 13 treated with antibiotics; the use of appropriate fluorochromes may enable selective identification of live bacteria and dead bacteria.

For analyses of this sort, particularly advantageous may be devices 10 provided with microfluidic arrangements that include a number of series of microchannels 13, such as the devices of FIGS. 12-15. These microfluidic techniques have a higher sensitivity as compared to other techniques (for example, turbidity), given that centrifugation "concentrates" the micro-organisms in a small space and hence renders them visible either in clear field with visible light, both in transmission and in reflection, or in fluorescence on marked cells. With the concentration technique proposed and an appropriate analysis of the image, either by means of linear arrays of sensors of by means of rectangular arrays of sensors (for example, CCD or CMOS cameras or any other technique used for image acquisition) a modification of +/−20% of the number of the cells is measured in a reliable and accurate way. Variations of this degree, which can be detected using the methodology proposed and instead cannot be detected using classic turbidity techniques, can be determined even after short growth times, for example comprised between 20 and 40 min. The quantification or estimation may be made, as has been said, via optical detections at least at the accumulation areas 15 of the various microchannels 13 of interest.

In addition or as an alternative, counting of the bacterial bodies can be carried out using electrodes set in the accumulation areas 15 in order to detect the modification of the impedance of an electrical field that contains a "proliferating" population of bacteria or microbes: this modification may be used as signal of the susceptibility (or resistance) of the bacterial strain under examination. Also in this case, the detection times may be extremely short.

The methodologies described above can be profitably used in situations that are extremely different from a clinical standpoint.

For instance, it is possible to measure the "absolute" number of bacteria or microbes in a sample of relatively common biological material (for example, urines for urinoculture). If, for example, a count higher than 100000 bacteria/mL is indicative of infection of the urinary ways, the mere "numerical" documentation of the bacterial charge indicates the pathological situation with great accuracy.

Also in the absence of identification of the microbe or bacterium (which can in any case be carried out with standard techniques, if necessary), the profile of susceptibility/resistance to an antibiotic panel may be easily evaluated, offering the patient the opportunity of undergoing a "non-empirical" treatment, but one based upon the study of the real antibiotic susceptibility. In this case, it is important to recall that the majority of positive urinocultures are characterised by a single isolated microbe, whereas polymicrobism is more frequent in hospitalised patients or, owing to pre-analytical causes, in patients that are complex for reasons linked to the sampling technique.

In a more complex situation (for example, in hospitalised patients), identification of the bacterium leads to an improvement in the strategies of treatment not only of the patient, but also of nosocomial infections that may be associated thereto. On the other hand, as has already been said, for less "noble" materials, like urines, identification of the pathogen can follow different pathways, whereas the profile of susceptibility to antibiotics that is not carried out in extremely short times could lead to a delay in setting up a life-saving antibiotic therapy. For this reason, the device 10 (in particular with micro-wells of the type as those designated by 16 in FIG. 16) could be loaded with a single colony (for example, isolated from a haemoculture), which has not yet been identified but for which an immediate therapeutic approach becomes necessary. In this latter case, bacteria isolated from complex materials may be seeded, and the antibiogram could be available within some tens of minutes.

From the foregoing description, the characteristics of the present invention are clear, as likewise are its advantages.

The devices and the methodologies proposed enable operation with relatively small starting volumes of sample, for example comprised between 0.05 and 1 mL. For instance, in paediatrics, in research conducted on small animals and in any case where it is useful to reduce the amount of (biological and reagent) material, also for economic reasons, it is advantageous to be able to use relatively small volumes. The measurement of a corpusculated component terminates when a number of particles are counted such as to render the problem of reproducibility virtually absent: in general 16000 particles are counted to obtain an accurate estimate of sub-populations that are represented by 1 to 5% of the total. Hence, if it is assumed, for example, to start from a concentration of one hundred thousand particles per millilitre, according to the invention an amount of starting sample comprised between 0.2 and 0.4 mL will be sufficient, whereas, for higher concentrations, for example one million particles per millilitre, the amount of starting sample may drop, for example, to between 0.02 and 0.06 mL.

The devices according to the invention are particularly advantageous for carrying out antibiograms.

In general terms, for this purpose, a bacteria culture can be inoculated into the microchannels 13 of at least one arrangement 12 of a device 10. The device 10 is then subjected to centrifugation (for example, using one of the devices 1 described), and the number of bacteria that have accumulated in the areas 15 of the microchannels 13 is then quantified or estimated. In applications of this sort, the microfluidic device 10 may be used exclusively for quantification of micro-organisms, for example bacteria, in so far as the proliferation in different conditions to be compared may be obtained previously, using ordinary laboratory equipment and devices.

In other applications, an antibiogram can be carried out starting from a two-dimensional culture of the bacteria on a solid support. In this case, the methodology may envisage the following steps:

i) taking a colony of bacteria from a solid-culture dish;
  ii) inoculating the colony or a part thereof into a liquid medium, for example a culture broth, preferably to form a homogeneous dispersion; and
  iii) loading the liquid medium containing the bacteria into the microchannels 13 of at least one arrangement 12 of a device 10, with at least some of the aforesaid microchannels that have been previously provided with antibiotics, preferably lyophilised antibiotics of different types and/or at different concentrations, and other microchannels that have not been provided with antibiotic;
  iv) incubating for a period of time ranging from 10 min to 6 h, preferably between 1 and 2 h;
  v) centrifuging the device 10; and
  vi) quantifying the bacteria that have accumulated in the areas 15 of the microchannels 13, in particular by carrying out a relative quantification between the microchannels 13 pre-treated with antibiotic and the ones not pre-treated, in order to obtain a profile of susceptibility of the bacteria in question to the antibiotic or antibiotics used.

Yet in other applications, the devices according to the invention can be advantageously used for carrying out an antibiogram starting from a primary sample, i.e., a sample taken directly from a subject or host organism (human or animal). In this case, the methodology may envisage the following steps:
  i) obtaining a concentrate or a mass (or pellet) of bacteria from the primary sample, for example urines; for this purpose, for example, the primary sample may be subjected to centrifugation, using ordinary laboratory equipment and devices in order to separate the aforesaid bacterial mass from the surfactant; centrifugation preferably is performed in two steps: a first step at low speed to eliminate the cells; and a second step at high speed to concentrate the bacteria; alternatively, the first centrifugation step can be replaced with a filtration to eliminate the cells;
  ii) inoculating the bacterial mass obtained or a part thereof into a liquid medium, for example a culture broth, preferably to form a homogeneous dispersion;
  iii) loading the liquid medium containing the bacteria into the microchannels 13 of at least one arrangement 12 of a device 10, with at least some of the aforesaid microchannels that have been previously provided with antibiotics, preferably lyophilised antibiotics of different types and/or at different concentrations, and other microchannels that have not been provided with antibiotic;
  iv) incubating for a period of time ranging from 10 min to 6 h, preferably between 1 and 2 h;
  v) centrifuging the device 10; and
  vi) quantifying the bacteria that have accumulated in the areas 15 of the microchannels 13, in particular by carrying out a relative quantification between the microchannels 13 pre-treated with antibiotic and the ones not pre-treated in order to obtain a profile of susceptibility of the bacteria in question to the antibiotic or antibiotics used.

It is clear that numerous variations may be made by the person skilled in the art to the supports and substrates, the devices, and the methods described herein by way of example, without thereby departing from the scope of the invention. It will likewise be evident to the person skilled in the art that individual characteristics described in relation to one embodiment may be used in other embodiments described herein, even different from the previous examples.

Application of the invention is not limited to the medical or veterinary sector, it being possible to use the supports and devices described for concentration and/or quantification of particles present in fluids of any type, for example also in the fields of industry or agriculture.

The invention claimed is:

1. A microfluidic device for concentrating and detecting particles contained in a fluid sample, the microfluidic device comprising:
  a substrate configured for being set in rotation with respect to a centre of rotation, the substrate having a surface at which at least one microfluidic arrangement is defined, which extends substantially according to a plane identified by the substrate, wherein the at least one microfluidic arrangement comprises a plurality of microchannels each having a first end and a second end; wherein
  each microchannel of the plurality of microchannels comprises, in a region thereof intermediate to the first end and the second end of the microchannel, at least one detection area that is at a first distance in a radial direction with respect to the centre of rotation of the substrate;
  the first end and the second end of each microchannel of the plurality of microchannels are at second distances in the radial direction with respect to the centre of rotation of the substrate;
  the first distance in the radial direction is greater than the second distances in the radial direction,
  wherein the at least one detection area is an area for particle accumulation;
  wherein the at least one microfluidic arrangement comprises a common loading duct or chamber and a common venting duct or chamber, all the microchannels of the plurality of microchannels being fluidically connected to the common loading duct or chamber and to the common venting duct or chamber, all the microchannels of the plurality of microchannels having the respective first ends and second ends fluidically connected in parallel to the common loading duct or chamber and to the common venting duct or chamber, respectively, the common loading duct or chamber being operable for receiving the fluid sample, such that the fluid sample can penetrate from the common loading duct or chamber into all the microchannels of the plurality of microchannels, and air contained in all the microchannels of the plurality of microchannels can progressively be vented at the common venting duct or chamber,
  wherein, in the at least one detection area for particle accumulation, each microchannel of the plurality of microchannels is substantially V-shaped or U-shaped, or comprises two substantially convergent microchannel branches, the at least one detection area of each microchannel of the plurality of microchannels being free of exit ways for the fluid sample,
  in such a way that particles contained in a volume of fluid of the fluid sample that penetrates into at least one microchannel of the plurality of microchannels concentrate in the at least one detection area as a result of the centrifugal force caused by a rotation of the substrate about the centre of rotation.

2. The microfluidic device according to claim 1, wherein the microchannels of the plurality of microchannels are arranged substantially side by side in the radial direction.

3. The microfluidic device according to claim 1, wherein each microchannel of the plurality of microchannels is shaped, at the respective at least one detection area, to define at least one of the following:
  at least one syphon,
  at least one well.

4. The microfluidic device according to claim 1, wherein each microchannel of the plurality of microchannels comprises at least one microchannel branch which extends in a substantially radial direction and leads to a respective one said detection area.

5. The microfluidic device according to claim 1, wherein each microchannel of the plurality of microchannels has associated at least two electrodes, the at least two electrodes being at one said detection area or in a position that is comprised between one said detection area and one of the first end and the second end of the corresponding microchannel of the plurality of microchannels.

6. The microfluidic device according to claim 1, wherein each microchannel of the plurality of microchannels:
  has a width of between 5 and 200 μm, and/or
  has a depth or height of between 2 and 100 μm.

7. The microfluidic device according to claim 1, wherein:
  each microchannel of the plurality of microchannels has at least one surface portion defined by at least one of a hydrophilic material or a hydrophobic material, the hydrophilic material or the hydrophobic material belonging to at least one of the substrate and a covering element of the device that extends at least partially over each microchannel of the plurality of microchannels.

8. The microfluidic device according to claim 1, wherein the substrate:
is configured for being mounted on a rotary member of a centrifugation device; and/or
is substantially disk-shaped.

9. The microfluidic device according to claim 1, wherein defined in said surface of the substrate are a plurality of said microfluidic arrangements arranged substantially aligned with one another in the radial direction and/or set substantially according to a circumference.

10. The microfluidic device according to claim 1, wherein said second distances are the same as one another.

11. A method for the detection of particles possibly present in a fluid sample, comprising the steps of:
providing the microfluidic device according to claim 1;
introducing a volume of the fluid sample into each microchannel of the at least one microfluidic arrangement of the microfluidic device;
causing a rotation of the microfluidic device with respect to the corresponding centre of rotation at a centrifugation speed; and
detecting particles that have accumulated in the area for particle accumulation of each microchannel, in an optical and/or electrical way.

12. A method for carrying out an antibiogram, comprising:
providing the microfluidic device according to claim 1;
providing a liquid medium containing micro-organisms, or microbes, or bacteria of at least one bacterial strain;
introducing a volume of the liquid medium into the plurality of first microchannels of the at least one first microfluidic arrangement of the microfluidic device;
causing an angular movement of the microfluidic device with respect to the corresponding centre of rotation at a centrifugation speed, via a centrifugation device; and
quantifying the number of micro-organisms, or microbes, or bacteria that have accumulated in the area for particle accumulation of each microchannel.

13. The method according to claim 12, comprising:
i) pre-treating said first microchannels with at least one first antibiotic;
ii) obtaining a mass of the micro-organisms, or the microbes, or the bacteria;
iii) inoculating at least one part of said mass into the liquid medium;
iv) introducing the volume of the liquid medium into said first microchannels;
v) waiting for a period of time comprised between 10 min and 6 h;
vi) subjecting the microfluidic device to centrifugation; and
vii) quantifying the number of micro-organisms, or microbes, or bacteria that have accumulated in the area for particle accumulation of said first microchannels, carrying out a relative quantification between said first microchannels and second microchannels of the microfluidic device that have not been pre-treated with the at least one first antibiotic, in order to obtain a susceptibility profile of said micro-organisms, or microbes, or bacteria to the at least one first antibiotic.

14. The method according to claim 13, wherein said mass referred to in step ii) is taken from a culture dish or else is obtained from a sample taken from a host organism.

15. A microfluidic device for concentrating and detecting particles contained in a fluid sample, the microfluidic device comprising:
a substrate configured for being set in rotation with respect to a centre of rotation, the substrate having a surface at which at least one microfluidic arrangement is defined, which extends substantially according to a plane identified by the substrate, wherein the at least one microfluidic arrangement comprises a plurality of microchannels each having a first end and a second end, wherein:
each microchannel of the plurality of microchannels comprises, in a region thereof intermediate to the first end and the second end, at least one detection area that is at a first distance in a radial direction with respect to the centre of rotation of the substrate;
the first end and the second end of each microchannel of the plurality of microchannels are at second distances in the radial direction with respect to the centre of rotation of the substrate;
the first distance in the radial direction is greater than the second distances in the radial direction,
wherein the at least one detection area is an area for particle accumulation;
wherein the at least one microfluidic arrangement comprises at least one first duct or chamber and a second duct or chamber, the microchannels of the plurality of microchannels having the respective first ends and second ends connected in parallel to the first duct or chamber and to the second duct or chamber, respectively, one of the first duct or chamber and second duct or chamber being pre-arranged for receiving the fluid sample, such that the fluid sample can penetrate from one end of the microchannels of the plurality of microchannels, and air contained therein can progressively be vented at the other one of the first duct or chamber and second duct or chamber,
wherein the microchannels of the plurality of microchannels are the same as one another and extend at least in part substantially parallel to, or equidistant from, one another in the radial direction,
wherein, in the at least one detection area for particle accumulation, each microchannel of the plurality of microchannels is substantially V-shaped or U-shaped, or comprises two substantially convergent microchannel branches, the at least one detection area of each microchannel of the plurality of microchannels being free of exit ways for the fluid sample,
in such a way that particles contained in a volume of fluid of the fluid sample that penetrates into at least one microchannel of the plurality of microchannels concentrate in the at least one detection area as a result of the centrifugal force caused by a rotation of the substrate about the centre of rotation.

* * * * *